(12) United States Patent
Ryd et al.

(10) Patent No.: US 11,529,237 B2
(45) Date of Patent: Dec. 20, 2022

(54) METHOD OF MANUFACTURING AN IMPLANT AND AN IMPLANT WITH TWO COATINGS

(71) Applicant: EPISURF IP-MANAGEMENT AB, Stockholm (SE)

(72) Inventors: Leif Ryd, Malmö (SE); Jeanette Spångberg, Skogås (SE); Katarina Flodström, Danderyd (SE)

(73) Assignee: Episurf IP-Management AB, Stockholm (SE)

( * ) Notice: Subject to any disclaimer, the term of this patent is extended or adjusted under 35 U.S.C. 154(b) by 0 days.

(21) Appl. No.: 16/490,914

(22) PCT Filed: Apr. 26, 2019

(86) PCT No.: PCT/EP2019/060721
§ 371 (c)(1),
(2) Date: Sep. 4, 2019

(87) PCT Pub. No.: WO2019/207099
PCT Pub. Date: Oct. 31, 2019

(65) Prior Publication Data
US 2021/0085468 A1 Mar. 25, 2021

(30) Foreign Application Priority Data
Apr. 27, 2018 (SE) .................... 1850520-6

(51) Int. Cl.
*A61F 2/38* (2006.01)
*A61F 2/30* (2006.01)
(Continued)

(52) U.S. Cl.
CPC ........ *A61F 2/30756* (2013.01); *A61F 2/3094* (2013.01); *A61F 2/30942* (2013.01);
(Continued)

(58) Field of Classification Search
CPC .. A61F 2/30756; A61F 2/3094; A61F 2/3092; A61F 2/4684; A61F 2/461;
(Continued)

(56) References Cited

U.S. PATENT DOCUMENTS 4,863,476 A 9/1989 Shepperd
5,370,700 A 12/1994 Sarkisian et al.
(Continued)

FOREIGN PATENT DOCUMENTS

EP 1 277 450 A2 1/2003
EP 1 698 307 A1 9/2006
(Continued)

OTHER PUBLICATIONS

Irena Gotman et al "Titanium Nitride-Based Coatings on Implantable Medical Devices" Advanced Biomaterials and Devices in Medicine pp. 53-73 (Year: 2014).*
(Continued)

*Primary Examiner* — Christopher D. Prone
(74) *Attorney, Agent, or Firm* — Faegre Drinker Biddle & Reath LLP

(57) ABSTRACT

The present invention relates to a medical implant for cartilage and/or bone repair at an articulating surface of a joint. The implant comprises a contoured implant body and at least one extending post. The implant body has an articulating surface configured to face the articulating part of the joint and a bone contact surface configured to face the bone structure of a joint, where the said articulating and bone contact surfaces face mutually opposite directions and said bone contact surface is provided with the extending post. A cartilage contact surface connects the articulating and the bone contact surfaces and is configured to contact the cartilage surrounding the implant body in a joint. The articulating surface has a layer that consists of titanium
(Continued)

nitride (TiN) as the wear-resistant material. The cartilage contact surface has a coating that substantially consists of a material having chondrointegration properties.

8 Claims, 6 Drawing Sheets

(51) Int. Cl.

| | | |
|---|---|---|
| B33Y 70/00 | (2020.01) | |
| B33Y 80/00 | (2015.01) | |
| B33Y 40/20 | (2020.01) | |
| B22F 10/00 | (2021.01) | |
| A61L 27/30 | (2006.01) | |
| A61L 27/32 | (2006.01) | |
| A61L 27/34 | (2006.01) | |
| A61L 27/54 | (2006.01) | |
| C23C 16/34 | (2006.01) | |
| C23C 16/50 | (2006.01) | |
| B33Y 10/00 | (2015.01) | |

(52) U.S. Cl.
CPC ............ *A61L 27/306* (2013.01); *A61L 27/32* (2013.01); *A61L 27/34* (2013.01); *A61L 27/54* (2013.01); *B22F 10/00* (2021.01); *B33Y 40/20* (2020.01); *B33Y 70/00* (2014.12); *B33Y 80/00* (2014.12); *C23C 16/34* (2013.01); *C23C 16/50* (2013.01); *A61F 2/3872* (2013.01); *A61F 2002/3006* (2013.01); *A61F 2002/30761* (2013.01); *A61F 2002/30948* (2013.01); *A61F 2002/30952* (2013.01); *A61F 2002/30985* (2013.01); *A61F 2310/00389* (2013.01); *A61F 2310/00407* (2013.01); *A61F 2310/00419* (2013.01); *A61F 2310/00928* (2013.01); *A61F 2310/00976* (2013.01); *A61F 2310/00982* (2013.01); *A61L 2300/412* (2013.01); *A61L 2420/02* (2013.01); *A61L 2430/06* (2013.01); *B33Y 10/00* (2014.12)

(58) Field of Classification Search
CPC .................. A61F 2/389; A61F 2/3859; A61F 2310/00976; A61F 2310/00928; A61F 2310/00407; A61F 2310/00389; A61L 27/32; A61L 2300/412; A61L 2420/00
See application file for complete search history.

(56) References Cited

U.S. PATENT DOCUMENTS

| | | | |
|---|---|---|---|
| 5,427,631 | A | 6/1995 | Johansson et al. |
| 5,702,448 | A | 12/1997 | Buechel et al. |
| 5,766,221 | A | 6/1998 | Benderev et al. |
| 5,938,686 | A | 8/1999 | Benderev et al. |
| 6,001,104 | A | 12/1999 | Benderev et al. |
| 6,261,322 | B1 | 7/2001 | Despres, III et al. |
| 6,306,142 | B1 | 10/2001 | Johanson et al. |
| 6,626,667 | B2 | 9/2003 | Sussman |
| 6,858,042 | B2 | 2/2005 | Nadler et al. |
| 7,160,331 | B2 | 1/2007 | Cooney, III et al. |
| 7,258,701 | B2 | 8/2007 | Aram et al. |
| 7,608,110 | B2 | 10/2009 | O'Driscoll et al. |
| 8,241,338 | B2 | 8/2012 | Castaneda et al. |
| 8,644,973 | B2 | 2/2014 | Bake et al. |
| 8,655,468 | B2 | 2/2014 | Bake et al. |
| 8,657,822 | B2 | 2/2014 | Bake et al. |
| 10,470,885 | B2 | 11/2019 | Bake et al. |
| 2002/0055783 | A1 | 5/2002 | Tallarida et al. |
| 2002/0082704 | A1 | 6/2002 | Cerundolo |
| 2003/0065400 | A1* | 4/2003 | Beam ............... C04B 35/638 623/23.51 |
| 2003/0100947 | A1 | 5/2003 | Nadler et al. |
| 2003/0216669 | A1 | 11/2003 | Lang et al. |
| 2004/0002766 | A1 | 1/2004 | Hunter et al. |
| 2004/0039447 | A1 | 2/2004 | Simon et al. |
| 2005/0049710 | A1 | 3/2005 | O'Driscoll et al. |
| 2005/0137600 | A1 | 6/2005 | Jacobs et al. |
| 2005/0164041 | A1 | 7/2005 | Dunsmore et al. |
| 2006/0190078 | A1 | 8/2006 | Fell |
| 2006/0198877 | A1 | 9/2006 | Steinwachs et al. |
| 2007/0021838 | A1 | 1/2007 | Dugas et al. |
| 2008/0195216 | A1 | 8/2008 | Philipp |
| 2008/0257363 | A1 | 10/2008 | Schoenefeld et al. |
| 2008/0312659 | A1 | 12/2008 | Metzger et al. |
| 2009/0209962 | A1 | 8/2009 | Jamali |
| 2009/0226068 | A1 | 9/2009 | Fitz et al. |
| 2009/0228104 | A1* | 9/2009 | Strzepa ............... A61F 2/30756 623/14.12 |
| 2009/0254093 | A1 | 10/2009 | White et al. |
| 2009/0254367 | A1 | 10/2009 | Belcher et al. |
| 2010/0268337 | A1 | 10/2010 | Gordon et al. |
| 2011/0125277 | A1 | 5/2011 | Nygren et al. |
| 2013/0073050 | A1 | 3/2013 | McEntire et al. |
| 2013/0110252 | A1* | 5/2013 | Bake .................. A61F 2/30756 623/23.57 |
| 2017/0100253 | A1 | 4/2017 | Bake et al. |
| 2018/0243096 | A1 | 8/2018 | Ryd et al. |
| 2020/0163771 | A1 | 5/2020 | Bake et al. |

FOREIGN PATENT DOCUMENTS

| | | |
|---|---|---|
| EP | 1 704 826 A1 | 9/2006 |
| EP | 2 116 210 A1 | 11/2009 |
| EP | 2 389 901 A1 | 11/2011 |
| JP | H8-173523 A | 7/1996 |
| JP | 2883214 | 4/1999 |
| JP | 2003-531657 | 10/2003 |
| JP | 2006-510403 A | 3/2006 |
| JP | 2008-188400 A | 8/2008 |
| JP | 2008-540057 | 11/2008 |
| JP | 2011-517579 A | 6/2011 |
| WO | WO-97/16137 A1 | 5/1997 |
| WO | WO-0143667 A1 | 6/2001 |
| WO | WO-01/82677 A2 | 11/2001 |
| WO | WO-2004/049981 A2 | 6/2004 |
| WO | WO-2004/075777 A2 | 9/2004 |
| WO | WO-2006/060416 A2 | 6/2006 |
| WO | WO-2006/091686 A2 | 8/2006 |
| WO | WO-2006/127486 | 11/2006 |
| WO | WO-2007/014164 A2 | 2/2007 |
| WO | WO-2007/092841 A2 | 8/2007 |
| WO | WO-2008/098061 A2 | 8/2008 |
| WO | WO-2008/101090 A2 | 8/2008 |
| WO | WO-2009/106816 A1 | 9/2009 |
| WO | WO-2009/108591 A1 | 9/2009 |
| WO | WO-2009/111624 A2 | 9/2009 |
| WO | WO-2009/111626 A2 | 9/2009 |
| WO | WO-2009/135889 A1 | 11/2009 |
| WO | WO-2010/114578 A1 | 10/2010 |
| WO | WO-2013/155500 A1 | 10/2013 |

OTHER PUBLICATIONS

Irena Gotman et al., "Titanium nitride-based coatings on implantable medical devices," Advanced Biomaterials and Devices in Medicine, 2014, pp. 53-73.

U.S. Appl. No. 16/676,583, Bake et al.

Notice of Reasons for Rejection dated Apr. 30, 2013 issued in corresponding Japanese patent application No. 2013-511655 (with English summary thereof) (3 pages).

English translation of an Office Action dated Jun. 4, 2013 issued in Japanese patent application No. 2013-511657 (2 pages).

English translation of a Summary of a Notice of Reasons for Rejection issued in corresponding Japanese patent application No. 2013-511656 dated Apr. 30, 2013 (1 page).

Office Action issued in Swedish patent application No. 1850520-6 dated Oct. 4, 2018.

(56) References Cited

OTHER PUBLICATIONS

International search report and written opinion dated Jul. 17, 2019 issued in international patent application No. PCT/EP2019/060721.

* cited by examiner

METHOD OF MANUFACTURING AN IMPLANT AND AN IMPLANT WITH TWO COATINGS

CROSS-REFERENCE TO PRIOR APPLICATIONS

This application is a § 371 National Stage Application of PCT International Application No. PCT/EP2019/060721 filed Apr. 26, 2019, which claims priority to Swedish Application No. 1850520-6 filed on Apr. 27, 2018, both of which are incorporated herein in their entirety.

FIELD OF THE INVENTION

This invention relates in general to the field of orthopedic implants. More particularly the present invention relates to a medical implant for cartilage and/or bone repair at an articulating surface in a joint such as a knee, ankle, hip, toe and shoulder. The present invention also relates to a method for manufacturing such an implant.

BACKGROUND

General Background

Traumatic and overuse disorders of the joints of the body is a common problem. The weight-bearing and articulating surfaces of for example knees and other joints, are covered with a layer of soft tissue that typically comprises a significant amount of hyaline cartilage. The cartilage is prone to damage due to disease, injury or chronic wear and such damage causes much suffering in terms of pain or disability to move freely. It is therefore important to have efficient means and methods for repairing damaged cartilage in joints in for example knees. Large knee prostheses on the market are successful in relieving pain but there is a limit in the lifetime of the prostheses of 10-20 years.

These large prostheses have lead to the further development of smaller implants that can be implanted with less invasive surgery. In this development there has also been an effort to achieve small joint implants, suitable for repair of a small or cartilage and bone cartilage injury that have a minimal influence on the surrounding parts of the joint. In the current development such small implants are designed as thin plates, or a head, with a hard surface for facing the articulating side of the joint and a bone contacting surface for facing the bone below the damaged part of cartilage. Generally, the shape and the curvature of the articulating, or articulate, surface of the implant are designed to be similar to the shape and the original, healthy curvature of the part of the joint where the implant is inserted. Such implants are often designed with a contoured surface head and may also have one or several extending posts in the shape of a peg or a rod projecting from the bone contacting side underneath the surface head for fastening the implant to the bone in a first fixation in connection with the implant surgery.

Specific Background

In the surgical operation of implanting such small implants it is critical that the implant is positioned in a precise manner, this first fixation is called the primary fixation and it provides a mechanical attachment of the implant directly after implantation. Primary mechanical fixation can be further reinforced with a secondary fixation of the implant to the bone tissue as the implant integrates with the underlying bone. A firm secondary fixation is promoted by coating the implant with an osteoinductive, bioactive material, for example hydroxyapatite, also called hydroxylapatite or HA, on the parts of the implant contacting the bone. The bone then grows into and/or onto the implant and is in this way fixated additionally to the bone. Although small implants have widened the repertoire for the orthopedic surgeons when it comes to repairing smaller cartilage damages in the joints, there are unwanted scenarios in the surgery of these small implants.

As an example, irregular formation on the articulating surface facing the cartilage surface of the opposing articulating part of the joint should be avoided as this irregular formation, in turn, may lead to irregular cartilage formation and wear damages to the cartilage on the opposing joint surface. Specifically, irregular formations, or irregularities, close to the peripheral edge of the articulating surface in the transition area between the articulating surface, which is facing opposing articulating part of the joint, and the neighboring cartilage contact surface, which is the side edge surface area of the implant facing cartilage surrounding the recess into which the implant is inserted, tend to lead to particularly severe irregular cartilage formation and wear damages to the cartilage on the opposing joint surface.

Further, when an implant is inserted to replace damaged cartilage in a joint, a small space may arise between a peripheral edge of the implant and the adjoining cartilage. It has been observed that joint fluid may enter the small space between the implant and the cartilage, and flow into gaps between the bone and the implant. This may lead to a stopped or delayed integration between the bone and the implant. It may even lead to the undermining of the implant and to the detachment of the implant. Another problem that may arise is that the cartilage in the immediate vicinity of the implant may slide in relation to the implant, such that it is twisted, slides over the edge onto the top of the implant or is pressed down such that the edge and surface of the implant projects above the surface of the cartilage. This in turn may lead to irregular cartilage formation and wear damages to both the cartilage in the vicinity of the implant and to the cartilage on the opposing joint surface.

Prior Art

U.S. Pat. No. 5,370,700 describes a femoral condyle device and a tibial plateau device which are mechanically attachable to femur and tibia, respectively, and which are preferably covered with a protective coating, e.g. of titanium nitride, for biocompatibility purposes and to provide an adequate bearing surface (column 2, line 24-30).

Examples of prior art which discloses implants where bioactive material is used on the bone contacting side of the implant to promote bone to grow onto the implant is found in the following patent publications:

EP2116210 A1 from Diamorph describes an implant component and a method for producing an implant using a functionally graded sintered material composed of at least 4 layers. A top layer comprises 100 wt % biocompatible wear resistant material whereas the bone contacting side of the implant comprises bioactive material, preferably hydroxyapatite (see FIG. 2 and the abstract). The functionally graded material between the top layer and the bone contacting side comprises gradually increasing amounts of bioactive material towards the bone contacting surface.

WO2009135889 A1 from Diamorph describes an implant device for an articulating surface in a joint such as a knee, elbow or shoulder. In this piece of prior art there is shown an implant that has a primary fixation means in the shape of an extending post that comprises bioactive ceramic material. Other surfaces comprising bioactive material are facing the bone underlying the cartilage (page 4 line 10-11).

WO2007/014164 A2 describes a method for implanting a prosthetic articular surface in a joint (e.g. a knee). Hydroxyapatite material (HA) is described as an alternative of a biocompatible and osteoinductive [046] material on the surface of the bone contacting portion of the implant [042], [045].

US2004/0002766 A1 relates to metallic orthopedic implants having surfaces of a thin, dense, highly wear-resistant coating of diffusion-hardened oxidation or nitridation layer in addition to surfaces coated with one or more bioceramic or bone growth promoting materials such as one or more apatite compounds. The apatite coating is applied on bone contacting areas. The publication shows that the bioceramics may be applied to different sites on the implant, and it is preferred that the bioceramics are applied to areas of maximum contact with bone, as it is intended to promote maximum bone in-growth and on-growth [0090].

EP 1277450 A2 shows a prosthetic implant for the repair and regeneration of tissue.

US 2017/0100253 describes a medical implant for cartilage repair at an articulating surface of a joint. The implant has a body consisting of titanium or a titanium-based alloy. The articulating surface may have an outer layer of wear-resistant material to achieve a more durable surface with a lower friction coefficient. In $D_1$, the bone contact surface of the implant, i.e. the surface facing the bone of the patient, may be provided with a bioactive material.

U.S. Pat. No. 5,427,631 describes the surface transformation of titanium to titanium nitride on protheses.

WO 2013/155500 relates to additive manufacturing of implants by aligning a design of the implant relative to a substrate in a manufacturing apparatus.

OBJECT OF THE INVENTION

General Object

The general object of the technology disclosed is to provide an implant for cartilage and/or bone repair at an articulating surface of a joint which has an articulating surface which is hard, durable and has a lower friction coefficient, both in the short term and in the long run. A further object of the technology disclosed is to provide an implant for cartilage and/or bone repair at an articulating surface of a joint that enables the articulating surface of the implant to preserve a lower friction coefficient also in the long-term to thereby enable the articulating surface of the implant interacting smoothly with the cartilage surface of the opposing articulating surface of the joint that the articulating surface of the implant is facing and occasionally is in direct contact with.

It is an object of the technology disclosed to provide a method of manufacturing an implant and an implant with better resistance to destabilization by mechanical agitation or shear forces.

A more specific object of the technology disclosed is to provide a method of manufacturing an implant and an implant with better adherence to surrounding cartilage and which is less prone to delamination and cracking. A further object and a problem solved by the technology disclosed is to provide an implant which has at least one of a harder and more durable articulating surface as well as an articulating surface with a lower friction coefficient than the material used for the implant body, both in the short term and in the long run.

Another object and a problem solved by the technology disclosed is to provide an implant with reduced risk of delamination of a coated layer of material coated on an articulating surface facing and occasionally being in contact with cartilage surface of an articulating part of a joint.

Another object of the technology disclosed is to provide a method of manufacturing an implant and an implant adapted for maintaining a smooth transition between its articulating surface and its cartilage contact surface, aiming to lead to much lesser wear on the opposing surface of the joint as the cartilage and the implant work as an integrated mechanical entity with better resistance to destabilization by mechanical agitation or shear forces.

It is a further object of the technology disclosed to reduce delamination, surface roughness and the number of irregular formations on the articulating surface facing the cartilage surface of the opposing articulating part of the joint as these irregularities, in turn, may lead to irregular cartilage formation and wear damages to the cartilage on the opposing joint surface. The risk of irregular formations, or irregularities, at the edge, or close to the edge in the transition area between the articulating surface and the neighboring cartilage contact surface, should particularly be reduced or mitigated as these irregular formations often tend to lead to more severe irregular cartilage formation and wear damages to the cartilage on the opposing joint surface.

Objectives of the technology disclosed include providing a method for manufacturing a medical implant and a medical implant adapted to provide lesser wear on the opposing surface of the joint in the short-term, but even more importantly in the long-term, in that the cartilage and the implant continue to work as an integrated mechanical entity which maintains better resistance to destabilization by mechanical agitation or shear forces.

Additionally, it is an object of the technology disclosed to provide a method for manufacturing a medical implant and a medical implant adapted to stimulate cartilage to grow into the implant by reducing or mitigating the risk of cracking and/or delamination of the articulating surface and the portion of the cartilage contact surface which is closest to the articulating surface, thereby achieving a smoother cartilage contact surface and an even firmer sealing and attachment of the implant to the cartilage contact surface. Yet another object of the technology disclosed is to provide an implant that is provided with a wear resistant articulating surface which is hard, durable and which has a lower friction coefficient and which is further provided with a side edge surface (cartilage contact surface (7)) having chondrointegration properties to promote cartilage on-growth to the side edge surface of the implant to be devised for long term fixation to the surrounding cartilage, thereby providing for an articulating surface which has a lower friction coefficient also in the long term.

A further object of the technology disclosed is to provide an implant that is provided with a wear resistant articulating surface which is harder, more durable and which has a lower friction coefficient than both other wear-resistant coatings and the material used for the implant body, and which is also further devised for long term fixation to the surrounding cartilage surface.

SUMMARY OF THE INVENTION

The technology disclosed relates to methods of manufacturing an implant and an implant for cartilage and/or bone repair at an articulating surface of a joint.

The technology disclosed aims at providing a method of manufacturing an implant and an implant with better adherence to surrounding cartilage and which is less prone to delamination and cracking.

The technology disclosed particularly aims at providing a method of manufacturing an implant and an implant with better resistance to destabilization by mechanical agitation or shear forces by coating the articulating surface of the implant with a wear-resistant material which is less prone to delamination in combination with coating the cartilage contact surface with a material with chondrointegration properties providing better adherence to surrounding cartilage.

The two coatings on the two separate, neighbouring surfaces according to the technology disclosed provides a first synergistic effect in that the smoothness of the articulating surface and in the transition between the cartilage contact surface and the articulating surface provided by coating the articulating surface with a wear-resistant material is even further improved by coating the cartilage contact surface with a coating material having chondrointegration properties.

The two coatings on the two separate, neighbouring surfaces according to the technology disclosed provides the second synergistic effect that the adherence of the cartilage contact surface to surrounding cartilage which is improved with coating the cartilage contact surface with a coating material with chondrointegration properties is even further improved by coating the articulating surface with a wear-resistant material (TiN) in that TiN as coating material is less prone to delamination and cracking than other wear-resistant coating materials.

The technology disclosed relates to methods of manufacturing an implant and a medical implant where the articulating surface 3 of the implant is provided with an outer layer of wear-resistant material having a lower friction coefficient and which is harder and more durable than the material used for the implant body 11 and the cartilage contact surface 7 of the implant is coated with a layer of material having chondrointegration properties.

The technology disclosed relates to methods of manufacturing an implant and a medical implant where the articulating surface of the implant is coated with a wear-resistant material consisting of titanium nitride (TiN) and the cartilage contact surface 7 of the implant is coated with a layer of material having chondrointegration properties.

The technology disclosed relates to methods of manufacturing an implant and a medical medical implant 1 for cartilage and/or bone repair at an articulating surface of a joint, comprising a contoured implant body 11 and at least one extending post 8, where said implant body has:
  a) an articulating surface 3 configured to face an articulating part of the joint;
  b) a bone contact surface 6 configured to face the bone structure of a joint, said articulating 3 and bone contact 6 surfaces facing mutually opposite directions; and
  c) a cartilage contact surface 7, which is a neighboring surface to the articulating surface 3 and connecting the articulating 3 and the bone contact 6 surfaces, and which is configured to contact the cartilage surrounding the implant body 11 in a joint, wherein the articulating surface 3 has an outer layer coating of wear-resistant material consisting of titanium nitride (TiN), and wherein said cartilage contact surface 7 is coated with a layer of material having chondrointegration properties for stimulating cartilage to grow into the implant surface.

The technology disclosed also relates to a method of manufacturing the medical implant 1 comprising:
  forming the implant body 11 of the implant 1, wherein the implant body 11 is consisting of titanium or a titanium-alloy;
  forming a wear-resistant layer on the articulating surface 3 of the implant body 11 of the medical implant 1 to make the articulating surface 3 harder and more durable, wherein said layer of wear-resistant material consists of titanium nitride (TiN) which is a coating material that adheres better to the titanium surface of the implant body 11 than other possible wear-resistant coatings, thereby mitigating the risk of cracking and/or delamination of the articulating surface 3 to provide a smoother transition to the cartilage contact surface 7; and
  forming a layer of material having chondrointegration properties on the cartilage contact surface 7 for stimulating cartilage to grow into the implant surface to achieve a firmer sealing and attachment of the implant, thereby providing a smoother transition between the cartilage and the implant leading to much lesser wear on the opposing surface of the joint as the cartilage and the implant work as an integrated mechanical entity with better resistance to destabilization by mechanical agitation or shear forces.

In embodiments, the technology disclosed relates to methods of manufacturing an implant and a medical implant 1 for cartilage and/or bone repair at an articulating surface of a joint, comprising a contoured implant body 11 and at least one extending post 8, where said implant body has:
  a) an articulating surface 3 configured to face an articulating part of the joint;
  b) a bone contact surface 6 configured to face the bone structure of a joint, where the bone contact surface 6 is provided with the at least one extending post (8), said articulating 3 and bone contact 6 surfaces facing mutually opposite directions; and
  c) a cartilage contact surface 7, which is a neighboring surface to the articulating surface 3 and connecting the articulating 3 and the bone contact 6 surfaces, and which is configured to contact the cartilage surrounding the implant body 11 in a joint, wherein the articulating surface 3 has an outer layer coating of wear-resistant material consisting of titanium nitride (TiN) which is a coating material that adheres better to the titanium surface of the implant body 11 than other possible wear-resistant coatings, thereby mitigating the risk of cracking and/or delamination of the articulating surface 3 to provide a smoother transition to the cartilage contact surface 7, and wherein said cartilage contact surface 7 is coated with a layer of material having chondrointegration properties for stimulating cartilage to grow into the implant surface.

In embodiments, the technology disclosed relates to methods of manufacturing an implant and a medical implant 1 for cartilage and/or bone repair at an articulating surface of a joint, comprising a contoured implant body 11 and at least one extending post 8, where said implant body has:
  a) an articulating surface 3 configured to face an articulating part of the joint;
  b) a bone contact surface 6 configured to face the bone structure of a joint, where the bone contact surface 6 is provided with the at least one extending post 8, said articulating 3 and bone contact 6 surfaces facing mutually opposite directions; and c) a cartilage contact surface 7, which is a neighboring surface to the articulating surface 3 and connecting the articulating 3 and the bone contact 6 surfaces, and which is configured to contact the cartilage surrounding the implant body 11 in a joint, wherein the articulating surface 3 has an outer layer coating of wear-resistant material which provides for a harder, more durable and smoother surface than can be achieved with the titanium or titanium-alloy material used for the implant body 11, wherein said wear-resistant material consists of titanium nitride (TiN) which is a coating material that adheres better to the titanium surface of the implant body 11 than other possible wear-resistant coatings, thereby mitigating the risk of cracking and/or delamination of the articulating surface 3 to provide a smoother transition to the cartilage contact surface 7, and wherein said cartilage contact surface 7 is coated with a layer of material having chondrointegration properties for stimulating cartilage to grow into the implant surface, providing the effect of providing a smoother transition between the articulating surface 3 cartilage contact surface 7 and the synergistic effect of achieving a better adherence of the wear-resistant material coated on the articulating surface 3 to the titanium surface of the implant body.

In embodiments, the technology disclosed relates to a medical implant 1 for cartilage and/or bone repair at an articulating surface of a joint, comprising a contoured implant body 11 and at least one extending post 8, where said implant body has:

a) an articulating surface 3 configured to face an articulating part of the joint;

b) a bone contact surface 6 configured to face the bone structure of a joint, where the bone contact surface 6 is provided with at least one extending post 8, said articulating 3 and bone contact 6 surfaces facing mutually opposite directions; and c) a cartilage contact surface 7, which is a neighboring surface to the articulating surface 3 and connecting the articulating 3 and the bone contact 6 surfaces, which is configured to contact the cartilage surrounding the implant body 11 in a joint, wherein the articulating surface 3 has an outer layer of wear-resistant material which is harder and more durable than the material used for the implant body 11, thereby providing a more even surface and a smoother transition to the neighboring cartilage contact surface 7, wherein said cartilage contact surface 7 is provided with a layer of material having chondrointegration properties for stimulating cartilage to grow into the implant surface, thereby providing a firmer sealing and attachment to the cartilage contact surface 7 and an even smoother transition to the neighboring articulating surface 3.

The layer of material having chondrointegration properties coated on the cartilage contact surface 7 for stimulating cartilage to grow into the implant surface also has the effect of providing a smoother transition between the articulating surface 3 cartilage contact surface 7.

In embodiments, the technology disclosed relates to method of manufacturing a medical implant 1, comprising:

forming the implant body 11 and the at least one extending post 8 of the implant 1, wherein the implant body 11 and the at least one extending post 8 is consisting of titanium or a titanium-alloy; and forming a wear-resistant layer on the articulating surface 3 of the implant body 11 of the medical implant 1, wherein said layer of wear-resistant material is harder and more durable than the material used for the implant body 11, thereby providing a more even surface and a smoother transition to the neighboring cartilage contact surface 7; and forming a layer of material having chondrointegration properties on at least a portion of the cartilage contact surface 7 for stimulating cartilage to grow into the implant surface to achieve a firmer sealing and attachment of the implant, thereby providing a smoother transition between the cartilage and the implant leading to much lesser wear on the opposing surface of the joint as the cartilage and the implant work as an integrated mechanical entity with better resistance to destabilization by mechanical agitation or shear forces.

The forming of a layer of material having chondrointegration properties on at least a portion of the cartilage contact surface 7 for stimulating cartilage to grow into the implant surface also has the effect of providing a smoother transition between the articulating surface 3 cartilage contact surface 7.

The implant of the technology disclosed comprises a contoured implant body 11, an articulating surface 3 adapted to face an articulating part of the joint, and a bone contact surface 6 adapted to face the bone structure of a joint. The articulating 3 and bone contact 6 surfaces of the implant are facing mutually opposite directions. The implant further comprises a cartilage contact surface 7 in form of a side edge surface, which is connecting the articulating 3 and the bone contact 6 surfaces. The cartilage contact surface 7 is adapted to contact the cartilage surrounding the implant body 11 in a joint. In embodiments, the bone contact surface 6 may be provided with at least one extending post 8.

In embodiments, at least a major portion of the upper portion of the cartilage contact surface 7 closest to the articulating surface 3 has a coating consisting of a material with chondrointegration properties to thereby be adapted for promoting improved cartilage integration with surrounding cartilage, which, in turn, provides a lower friction coefficient for the surface area of the articulating surface 3 closest to the cartilage surface also in the long run.

In embodiments, the cartilage surface 7 coated or partly coated with a layer of material having chondrointegration properties adapted for promoting integration with surrounding cartilage, where the material having chondrointegration properties is any of hydroxyapatite (HA), bone morphogenetic protein (BMP), beta tricalcium phosphate (TCP), alfa tricalcium phosphate (TCP), collagens, fibronectin, osteonectin, calcium sulphate, calcium phosphate, calcium aluminates, calcium silicates, calcium carbonates, fluoro compounds, or combinations thereof, and where the material with chondrointegration properties is capable of stimulating cartilage growth and regeneration.

In certain embodiments, the bone contact surface 6 of the implant 1 is coated or partly coated with a third layer of material having osseointegration properties, thereby promoting, or stimulating, bone growth and regeneration.

In embodiments of the technology disclosed, the implant is provided with a first layer of material on a major portion of the articulating surface to provide a lower friction coefficient on the articulating surface and a second layer of material having chondrointegration properties, different from the first layer of material, on the surface area of the side edge surface of the implant, i.e. on the surface area of the cartilage contact surface 7.

In embodiments of the technology disclosed, the implant is provided with a first layer of material on a major portion of the articulating surface to provide a lower friction coefficient on the articulating surface and a second layer of material having chondrointegration properties, different from the first layer of material, on at least 50% of the upper half portion of the cartilage contact surface area closest to the articulating surface 3 of the implant.

In embodiments of the technology disclosed, the implant is provided with a first layer of material on a major portion of the articulating surface to provide a lower friction coefficient on the articulating surface and a second layer of material having chondrointegration properties, different from the first layer of material, on at least 80% of the upper half portion of the cartilage contact surface area closest to the articulating surface 3 of the implant.

In certain aspects, the technology disclosed is based on the further findings that titanium or titanium-alloys, but for some applications also polyether ether ketone (PEEK), are preferred material for the implant body and the at least one extending peg of an implant since these are materials which are well-proven clinically, have some osseointegration or chondrointegration properties in order to function as a back-up to a coated osseointegration/chondrointegration layer, and are, to different degrees, also suitable material for use in a 3D printing process for manufacturing the implant, thereby being suitable to be use as the material for manufacturing at least one of the implant body and the extending peg of an implant.

However, titanium and titanium-alloys are less suitable to be used as the material for an articulating surface of an implant which is facing and, at least occasionally, is in contact with the cartilage surface of an articulating part of a joint. The inventors have found that if titanium or a titanium-alloy is used as the material for the implant body, the articulating surface of the implant body facing an articulating part of a joint needs to be provided with a harder and more wear-resistant material than titanium. In embodiments, the preferred material for the articulating surface 3 of an implant body 11 when the implant body 11 is made of titanium, or a titanium-alloy, is titanium nitride (TiN). Titanium nitride (TiN) is a wear-resistant material which is harder and provides a more durable surface than titanium, further titanium nitride has a lower friction coefficient than titanium and is therefore more suitable as material for the articulating surface 3 facing, and occasionally in contact with, a cartilage surface of the articulating part of the joint. Furthermore, if titanium nitride (TiN) is coated on a surface of titanium, it adheres better than other possible wear-resistant coatings and the risk of cracking and/or delamination of a wear-resistant layer provided on an articulating surface of an implant made of titanium is mitigated by using a coating material consisting of titanium nitride (TiN).

In a first aspect, the inventive concept comprises a medical implant 1 for cartilage and/or bone repair at an articulating surface of a joint, comprising a contoured implant body 11 and at least one extending post 8. The implant body has an articulating surface 3 configured to face the articulating part of the joint and a bone contact surface 6 configured to face the bone structure of a joint, where the bone contact surface 6 is provided with an extending post 8 and said articulating surface 3 and bone contact 6 surfaces face mutually opposite directions. A cartilage contact surface 7 connects the articulating 3 and the bone contact 6 surfaces and is configured to contact the cartilage surrounding the implant body 11 in a joint. The articulating surface 3 of the implant is provided with a wear-resistant layer. In embodiments, e.g. when titanium is the chosen material for the implant body of the implant, this wear-resistant layer consists of titanium nitride (TiN).

In embodiments, the invention provides an implant with an implant body consisting of titanium and which is provided with a thin layer of titanium nitride on its articulating surface. The layer of titanium nitride provides the implant with a thin, dense, low friction, wear resistant, biocompatible surface ideally suited for use on an articulating surface of the implant facing an opposing articulating part of a joint. The articulating part, or parts, of the joint occasionally at least one of articulates, translates or rotates against the articulating surface of the implant. A thin layer of titanium nitride, e.g. applied by surface coating, has been identified to be in particular usefully employed on the articulating surface of an implant when the implant consists of titanium or a titanium-alloy. A titanium implant with titanium nitride layer coated on its articulating surface 3 yields a durable long-lasting use of the implant when inserted in a joint.

The present invention relates to a medical implant 1 for cartilage and/or bone repair at an articulating surface of a joint is provided. In embodiments, the medical implant comprises a contoured implant body 11, and at least one extending post 8, where said implant body has:

a) an articulating surface 3 configured to face an articulating part of the joint;

b) a bone contact surface 6 configured to face the bone structure of a joint, where the bone contact surface 6 is provided with at least one extending post 8, said articulating 3 and bone contact 6 surfaces facing mutually opposite directions; and c) a cartilage contact surface 7, connecting the articulating 3 and the bone contact 6 surfaces, which is configured to contact the cartilage surrounding the implant body 11 in a joint, wherein the articulating surface 3 is at least one of modified and coated with a layer of wear-resistant material which is harder and more durable than the material used for the implant body 11.

In embodiments when the wear-resistant layer is coated on the articulating surface 3, the thickness of the wear-resistant layer is below 50 micrometer, preferably below 20 micrometer. The reason is that, if the wear-resistant layer is thicker than 50 micrometer, cracking and/or delamination of the coated surface may occur.

In embodiments, the implant body 11 of the above medical implant 1 consists of titanium (Ti), or a titanium-alloy, and the articulating surface 3 is provided with a wear-resistant layer in form of a layer of titanium nitride (TiN), which adheres strongly to titanium and titanium-alloys, thereby providing for an articulating surface 3 which is suitable for being occasionally in contact with the cartilage surface of an opposing articulating part of the joint.

In embodiments, the cartilage surface 7 of the above medical implant 1 has a coating consisting of material, where the bioactive material is hydroxyapatite (HA).

In embodiments, the cartilage surface 7 of the above medical implant 1 has a coating consisting of bioactive material, where the bioactive material is any of hydroxyapatite (HA), bone morphogenetic protein (BMP), beta tricalcium phosphate (TCP), alfa tricalcium phosphate (TCP), collagens, fibronectin, osteonectin, calcium sulphate, calcium phosphate, calcium aluminates, calcium silicates, calcium carbonates or bioactive glass, fluoro compounds or combinations thereof.

The invention is also based on the findings that some bioactive substances, e.g. hydroxyapatite (HA), bone morphogenetic protein (BMP), beta tricalcium phosphate (TCP) or alfa tricalcium phosphate (TCP) have the ability to stimulate cartilage growth and regeneration, in addition to the previously well known ability to stimulate growth in bone tissue. In order to solve the above stated problems the inventors have designed an implant with a cartilage contacting rim coated with a bioactive material, e.g. HA, TCP and/or BMP, and thereby achieved an implant with a potential for better fixation in the joint, sealing of the interface between the implant and the cartilage and a better clinical outcome. In a second aspect, the inventive concept also comprises a medical implant 1 for cartilage and underlying bone repair at an articulating surface of a joint, comprising a contoured implant body 11 and at least one extending post 8. The implant body has an articulating surface 3 configured to face the opposing articulating part of the joint and a bone contact surface 6 configured to face the bone structure of a joint, where the bone contact surface 6 is provided with the at least one extending post 8 and said articulating 3 and bone contact 6 surfaces face mutually opposite directions. A cartilage contact surface 7 connects the articulating 3 and the bone contact 6 surfaces and is configured to contact the cartilage surrounding the implant body 11 in a joint. The cartilage contact surface 7 has a coating substantially consisting of a bioactive material. In embodiments of the invention, the bioactive material is any of hydroxyapatite (HA), titanium alloys, bone morphogenetic protein (BMP), beta tricalcium phosphate (TCP), collagens, fibronectin, osteonectin, calcium sulphate, calcium phosphate, calcium aluminates, calcium silicates, calcium carbonates or bioactive glass, or combinations thereof. In an aspect of the invention the bioactive material is capable of stimulating cartilage growth and regeneration. Preferably the bioactive material is any of hydroxyapatite (HA), bone morphogenetic protein (BMP) and/or beta tricalcium phosphate (TCP), most preferably the bioactive material is hydroxyapatite (HA).

Further varieties of the inventive concept comprise such an implant comprising any of the following optional individual or combinable aspects:

The bone contact surface 6 is coated or partly coated with bioactive material.

The extending post is coated or partly coated with bioactive material.

The bioactive material of the bone contact surface 6 and or the at least one extending post 8 is any of hydroxyapatite (HA), bone morphogenetic protein (BMP), beta tricalcium phosphate (TCP), collagens, fibronectin, osteonectin, calcium sulphate, calcium phosphate, calcium aluminates, calcium silicates, calcium carbonates, bioactive glass or bisphosphonates, or combinations thereof.

In embodiments, at least portions of the at least one extending post is not coated with bioactive material.

The articulating surface (3) substantially corresponds to the curvature of the original articulating surface at the site of the diseased cartilage, prior to damage.

The coating of the cartilage contact surface (7) and/or bone contact surface (6) and/or extending post (8) consists of more than 95% hydroxyapatite according to X-ray Diffraction (XRD) analysis.

The bone contact surface or the cartilage contact surface or both has a double coating, comprising an inner coating and a surface coating of hydroxyapatite and/or tricalcium phosphate.

The present invention is also related to a method of manufacturing a medical implant comprising a contoured, substantially plate shaped implant body 11 and at least one extending post 8. The implant body has an articulating surface 3 configured to face the opposing articulating part of the joint and a bone contact surface 6 configured to face the bone structure of a joint, where the bone contact surface 6 is provided with the at least one extending post 8 and said articulating 3 and bone contact 6 surfaces face mutually opposite directions. In embodiments, the method of manufacturing the above medical implant (1) comprises:

forming the implant body 11 of the implant 1 consisting of titanium or a titanium-alloy; and forming a wear-resistant layer on the articulating surface (3) of the implant body (11) of the medical implant (1), thereby making the articulating surface 3 harder and more durable.

In embodiments, the above method of manufacturing a medical implant further comprises:

coating a layer of bioactive material on at least one of a bone contact surface 6, a cartilage contact surface 7 and at least portions of at least one extending post 8 of the medical implant 1.

In embodiments, the present invention relates to a method for manufacturing a medical implant 1 by manufacturing at least one of the implant body 11 and the at least one extending post 8 of the medical implant 1, preferably based on design parameters, said manufacturing of the medical implant 1 comprises:

forming a wear-resistant layer on the articulating surface 3 of the implant body 11 of the medical implant 1, where the purpose is to make the articulating surface 3 harder and more durable, and forming a bioactive layer on at least one of a bone contact surface 6, a cartilage contact surface 7 and at least portions of at least one extending post 8 of the medical implant 1, where the purpose is to improve the osseo (bone)- and chondrointegration (integration to cartilage) properties of the surface(s).

In embodiments, the manufacturing of the above medical implant 1 comprises manufacturing at least portions of at least one of the implant body 11 and the at least one extending post 8 of the medical implant 1, preferably based on design parameters, where said manufacturing of the medical implant 1 includes forming a layer of wear-resistant layer on the articulate surface 3 of the implant body 11 of the medical implant 1 for the purpose of making the articulate surface 3 harder and more durable.

BRIEF DESCRIPTION OF THE FIGURES

The present invention will be further explained below with reference to the accompanying drawings, in which.

DETAILED DESCRIPTION OF THE INVENTION

Introduction

Figure 1A:
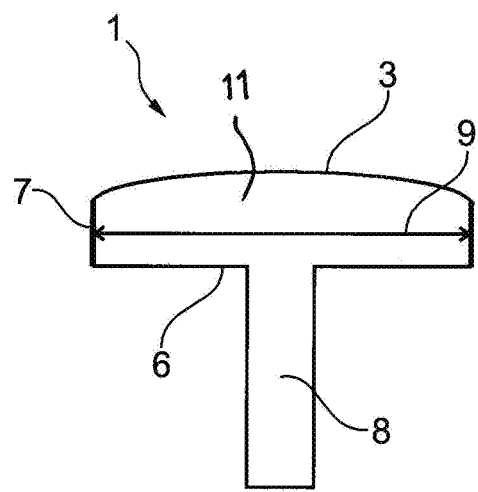
FIG. 1a is shows a sectional view of an exemplifying embodiment of the implant of the present invention with the articulating surface coated with a wear-resistant surface such as titanium nitride (TiN).
Figure 1B:
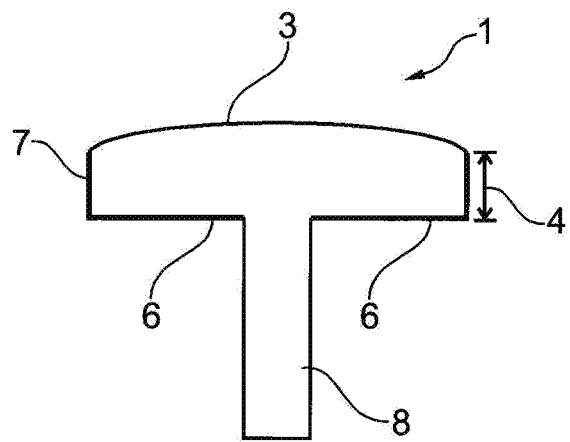
FIG. 1b shows a sectional view of an exemplifying embodiment of the implant of the present invention with the articulating surface 3 coated with titanium nitride (TiN) and the cartilage contact surfaces coated with hydroxyapatite.
Figure 1C:
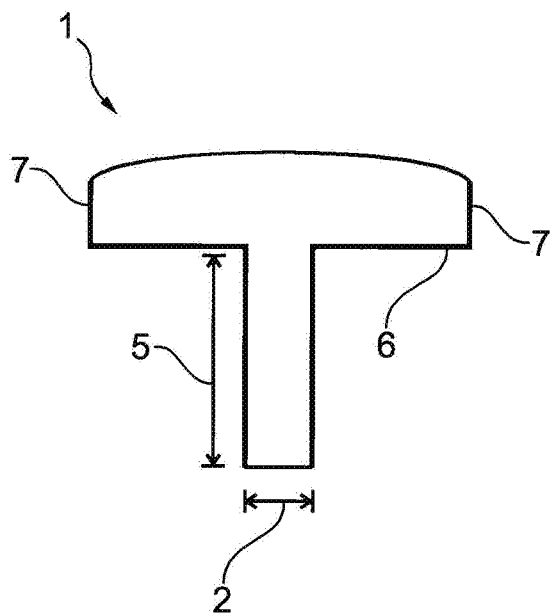
FIG. 1c shows a sectional view of an exemplifying embodiment of the implant of the present invention with the articulating surface 3 coated with titanium nitride (TiN) and the bone contact and the cartilage contact surface and also portions of the extending post coated with hydroxyapatite.
Figure 1D:
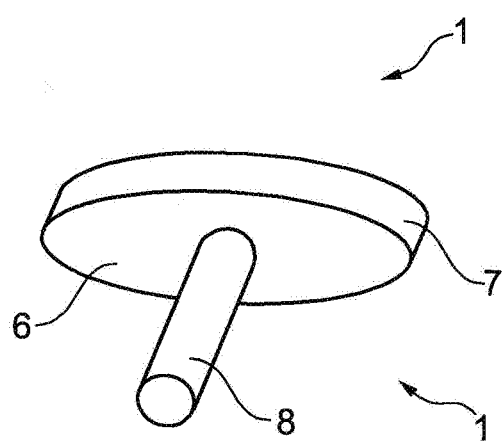
FIG. 1d shows a perspective view of an implant and shows an embodiment of the present invention having a hydroxyapatite coating on the cartilage contact surface.
Figure 2:
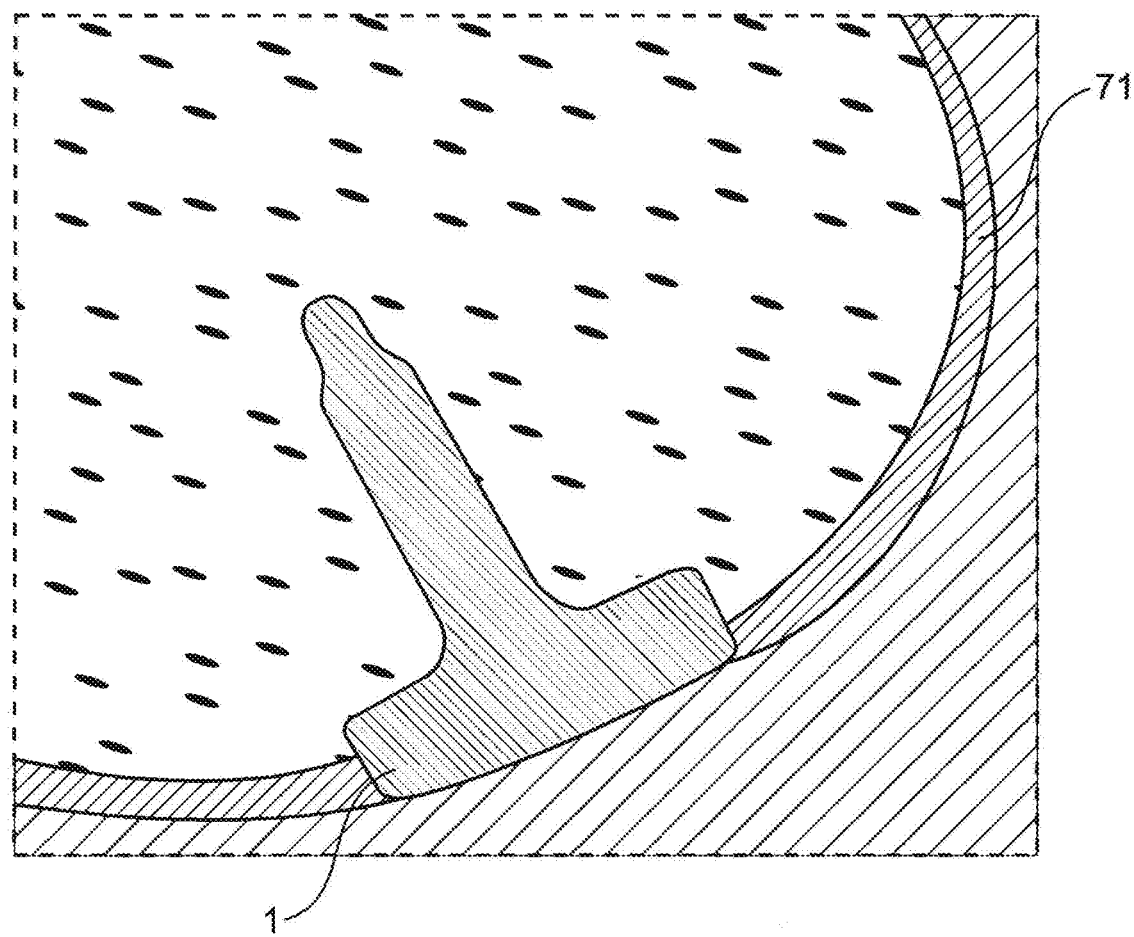
FIG. 2 shows a schematic view of the coated implant according to the invention inserted in the bone and cartilage surface of a joint.
Figure 3:
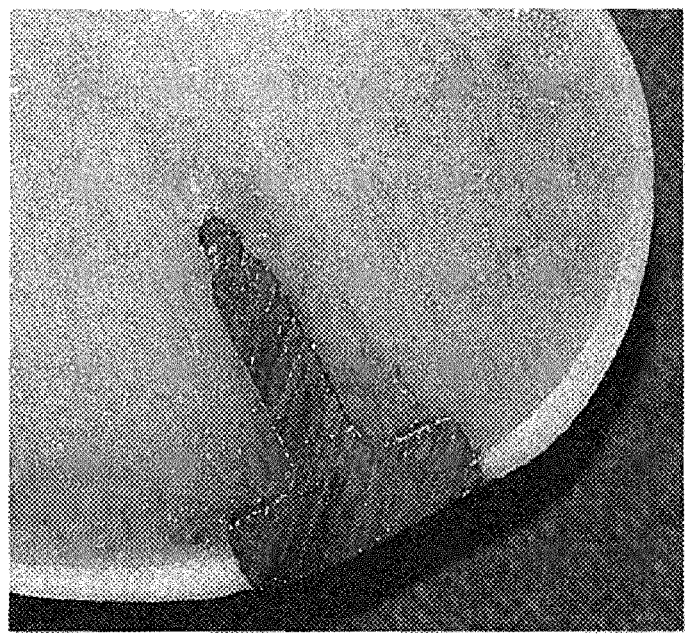
FIG. 3 shows a photo of the coated implant according to the invention inserted in the bone and cartilage surface of a joint.
Figure 4:
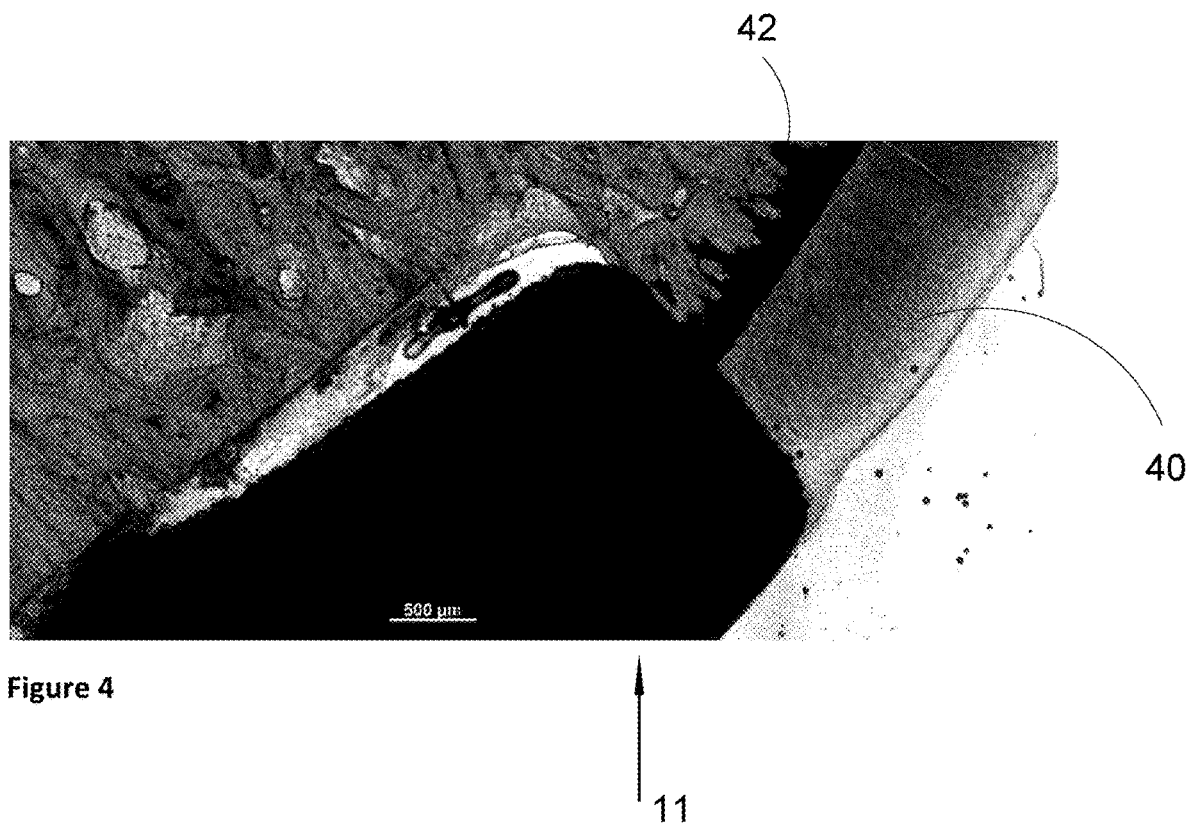
FIG. 4 shows a close up view in a photo of the coated implant according to the invention inserted in the bone and cartilage surface of a joint.
Figure 5:
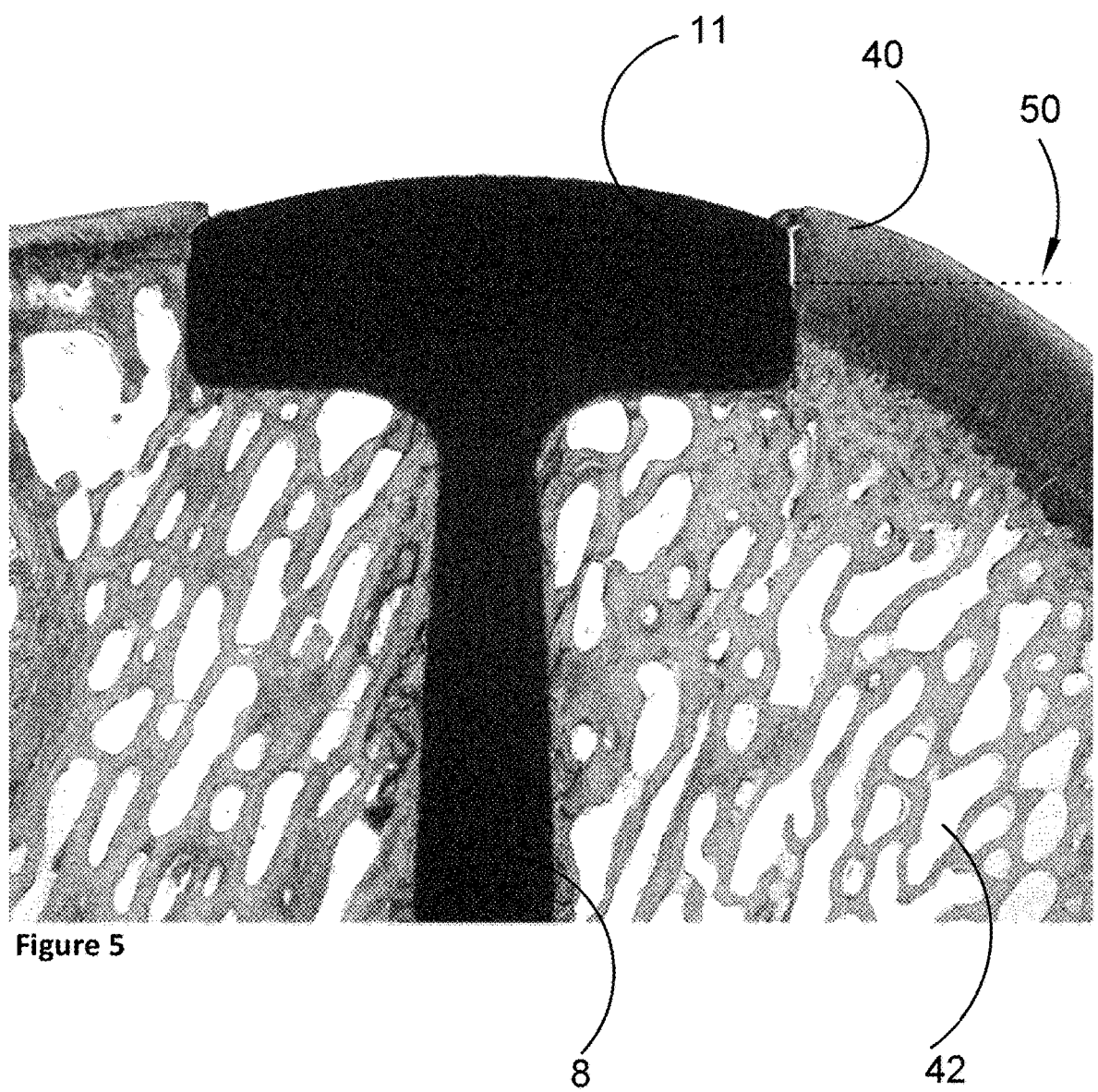
FIG. 5 shows a photo of the coated implant according to the invention inserted in the bone and cartilage surface of a joint.
Figure 6:
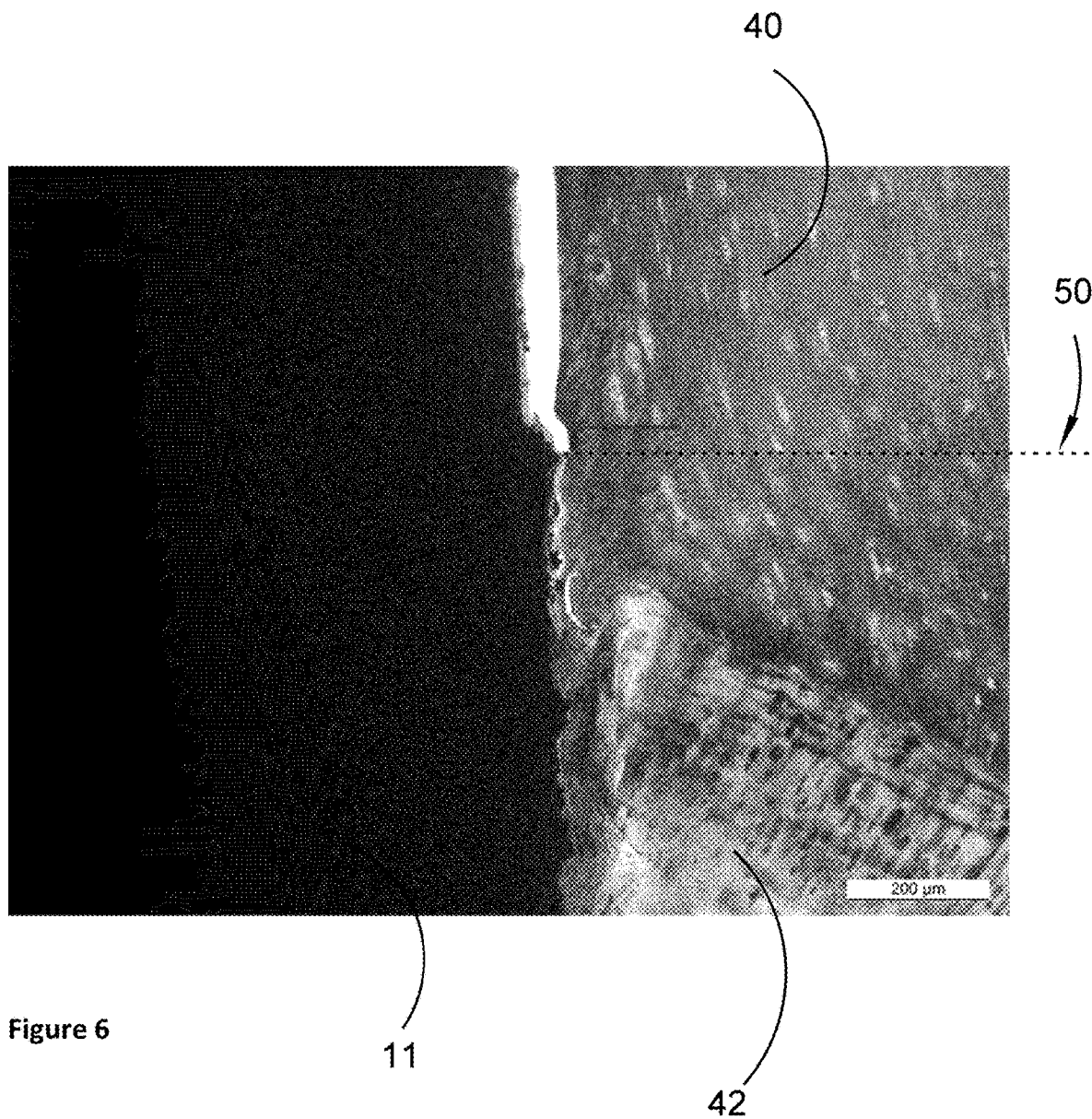
FIG. 6 shows a photo of the coated implant according to the invention inserted in the bone and cartilage surface of a joint.

It has been observed that friction in the interface surface between the articulating surface of an implant facing the cartilage surface of the opposing articulating part of the joint causes wear on the cartilage surface due to shear from the relative movement of the opposing articulating part and the implant. This wear may cause irregular formation on the articulating surface of the implant. This in turn may lead to irregular cartilage formation and wear damages to the cartilage of the opposed articulating part of the joint.

An object of the technology disclosed is to provide a method of manufacturing an implant and an implant designed to reduce or mitigate the risk of cracking and/or delamination of the articulating surface. According to the technology disclosed, this is at least partly achieved by coating the articulating surface 3 of the implant with a wear-resistant material consisting of titanium nitride (TiN), thereby also providing for a smoother transition between the cartilage and the implant leading to much lesser wear on the opposing surface of the joint as the cartilage and the implant work as an integrated mechanical entity with better resistance to destabilization by mechanical agitation or shear forces. Titanium nitride (TiN) is a coating material that adheres better to a titanium surface of an implant body than other possible wear-resistant coatings. The further effect of this is that a coating with titanium nitride (TiN) is less prone to delamination and/or cracking than other possible wear-resistant coating materials.

Yet another object of the technology disclosed is to provide a method of manufacturing an implant and an implant designed to achieve a firmer sealing and attachment of the implant to the surrounding cartilage. According to the technology disclosed, this is at least partly achieved by providing a layer of material having chondrointegration properties, thereby also providing for a smoother transition between the cartilage and the implant leading to much lesser wear on the opposing surface of the joint as the cartilage and the implant work as an integrated mechanical entity with better resistance to destabilization by mechanical agitation or shear forces.

The technology disclosed aims at providing a method of manufacturing an implant and an implant with better adherence to surrounding cartilage and which is less prone to delamination and cracking, which, in turn, leads to much lesser wear on the opposing surface of the joint.

The technology disclosed particularly aims at providing a method of manufacturing an implant and an implant with better resistance to destabilization by mechanical agitation or shear forces by coating the articulating surface of the implant with a wear-resistant material which is less prone to delamination in combination with coating the cartilage contact surface with a material with chondrointegration properties providing better adherence to surrounding cartilage.

The two coatings on the two separate, neighbouring surfaces according to the technology disclosed provides a first synergistic effect in that the smoothness of the articulating surface and in the transition between the cartilage contact surface and the articulating surface provided by coating the articulating surface with a wear-resistant material is even further improved by coating the cartilage contact surface with a coating material having chondrointegration properties.

The two coatings on the two separate, neighbouring surfaces according to the technology disclosed provides the second synergistic effect that the adherence of the cartilage contact surface to surrounding cartilage which is improved with coating the cartilage contact surface with a coating material with chondrointegration properties is even further improved by coating the articulating surface with a wear-resistant material of titanium nitride (TiN) in that TiN as a coating material is less prone to delamination and cracking than other wear-resistant coating materials.

The technology disclosed is aimed at reducing surface roughness and the number of irregular formations on the articulating surface facing the cartilage surface of the opposing articulating part of the joint as these irregularities, in turn, may lead to irregular cartilage formation and wear damages to the cartilage on the opposing joint surface. The risk of irregular formations, or irregularities, at the peripheral edge, or close to the edge in the transition area between the articulating surface 3 and the neighboring cartilage contact surface 7, should particularly be reduced/mitigated as these irregular formations often tend to lead to more severe irregular cartilage formation and wear damages to the cartilage on the opposing joint surface.

The technology disclosed provides a method for manufacturing a medical implant and a medical implant adapted to provide lesser wear on the opposing surface of the joint also in the long-term because the cartilage and the implant continue to work as an integrated mechanical entity which maintains better resistance to destabilization by mechanical agitation or shear forces. Specifically, the technology disclosed to provides an even smoother transition between the cartilage contact surface and the articulating surface of the implant by achieving a firmer sealing and attachment of the cartilage contact surface to the surrounding cartilage, thereby maintaining the excellent adherence provided by a wear-resistant coating consisting of titanium nitride (TiN), which, in turn, leads to a much lesser wear on the opposing surface of the joint as the cartilage and that the implant work as an integrated mechanical entity, and also continue to work as an integrated mechanical entity in the long-term with better resistance to destabilization by mechanical agitation or shear forces.

The technology disclosed particularly provides an even smoother transition between the cartilage contact surface and the articulating surface of the implant to thereby maintain the excellent adherence provided by a wear-resistant coating consisting of titanium nitride (TiN), leading to a much lesser wear on the opposing surface of the joint as the cartilage and that the implant continues to work as an integrated mechanical entity also in the long-term with better resistance to destabilization by mechanical agitation or shear forces.

According to the technology disclosed, the smoother transition between the cartilage contact surface and the articulating surface is achieved by selecting titanium nitride (TiN) as the wear-resistant coating material for better adherence of the wear-resistant coating on the articulating surface and providing a layer of material having chondrointegration properties on the cartilage contact surface to provide for firmer sealing and attachment of the cartilage contact surface of the implant to the surrounding cartilage.

The technology disclosed provides a method for manufacturing a medical implant and a medical implant adapted to stimulate cartilage to grow into the implant by mitigating the risk of cracking and/or delamination, thereby achieving a smoother cartilage contact surface and an even firmer sealing and attachment of the implant to the cartilage contact surface to provide an implant with better resistance to destabilization by mechanical agitation or shear forces.

Specifically, the technology disclosed provides an even smoother transition between the cartilage contact surface and the articulating surface of the implant by proposing coating the cartilage contact surface with a layer of material having chondrointegration properties with the purpose of both improving and maintaining the excellent adherence achieved by a wear-resistant coating consisting of titanium nitride (TiN), which, in turn, leads to a much lesser wear on the opposing surface of the joint as the cartilage in that the implant works as an integrated mechanical entity, and continues to work as an integrated mechanical entity in the long-term.

The selection of titanium nitride (TiN) as the wear-resistant coating material achieves the effect of a better adherence of the wear-resistant coating to the articulating surface and the introduction of a layer of material having chondrointegration properties on the cartilage contact surface achieves the effect of a firmer sealing and attachment of the cartilage contact surface of the implant to the surrounding cartilage. Both these two distinguishing features of the technology disclosed each improves the effect provided by the other distinguishing feature, thereby providing synergistic, or combinative, effects of an improved (even better) adherence of the wear-resistant coating and an improved (even firmer) sealing and attachment of the cartilage contact surface to the surrounding cartilage, respectively. The two distinguishing features of the technology disclosed thereby also both contributing to the combinative effect of an even smoother transition/edge between the articulating surface and the cartilage contact surface of the implant, particularly in the long-term, with the purpose of that the implant continues to work as an integrated mechanical entity, with better resistance to destabilization by mechanical agitation or shear forces.

The present invention addresses these problems related to wear and irregular formation on the articulating surface of the implant by proposing a new type of medical implant for replacing or repairing damaged, diseased or injured cartilage in an articulating surface of a joint. The implant is having an articulating surface 3 facing an articulating part of a joint, and is configured to occasionally be in contact the cartilage in the opposed articulating part of a joint. According to technology disclosed, the articulating surface 3 is provided with a layer of wear-resistant material. The proposed new implant, and the proposed new methods for manufacturing the new implant, aims at mitigating problems related to long-term wear issues of the articulating surface of an implant, by providing a layer of wear-resistant material on an implant's articulating surface which is facing the cartilage surface of an opposing articulating part of a joint. By providing the layer of wear-resistant material according to the technology disclosed, the articulating surface of the implant becomes harder and more durable to shear from the movement of the cartilage surface of the articulating part of the joint surface, yielding a smoother interaction between the articulating surface of the implant and the cartilage surface of the opposing articulating part of the joint the articulating surface is facing.

The technology disclosed proposes coating a layer of wear-resistant material consisting of titanium nitride (TiN), rather than other possible wear-resistant coatings, on the articulating surface 3 to mitigate the risk of cracking and/or delamination of the articulating surface (and the upper portion of the cartilage contact surface 7) at the peripheral edge of the articulating surface in the long-term, thereby providing a smoother transition/edge between the articulating surface and the cartilage contact surface 7 in the long-term. Achieving a smoother transition between the articulating surface 3 and the cartilage contact surface 7 by coating the articulating surface 3 with a titanium nitride (TiN) coating in turn has a synergistic effect in that the effect of the firmer sealing and attachment provided by the layer of material having chondrointegration properties coated on the cartilage contact surface is further improved.

Furthermore, coating a layer of material having chondrointegration properties on the cartilage contact surface 7 to achieve a firmer sealing and attachment of the implant to the surrounding cartilage also provides for a smoother transition between the articulating surface and the cartilage contact surface 7 in the long-term. Achieving a smoother transition between the articulating surface 3 and the cartilage contact surface 7 by coating a layer of material having chondrointegration properties on the cartilage contact surface 7 in turn provides the synergistic effect that the long-term effect of mitigating the risk of cracking and/or delamination of the articulating surface 3 by coating the articulating surface 3 with a titanium nitride (TiN) coating is further improved as the upper portion of the cartilage contact surface adheres better to the surrounding cartilage, thereby reducing the long-term risk of cracking and/or delamination of the articulating surface 3.

The wear resistant layer provided on the articulating surface 3 is chosen to provide a wear resistant surface which is durable and resistant to the abrasive forces acting upon it as it articulates and moves in relation to the surrounding parts of the joint. When pure titanium, or a titanium-alloy, is chosen as the material for the implant body 11, a layer of titanium nitride (TiN) is preferably provided on the articulating surface 3 of the implant body 11.

The technology disclosed relates to methods of manufacturing an implant and a medical implant where the articulating surface of the implant is coated with a wear-resistant material consisting of titanium nitride (TiN) and the cartilage contact surface of the implant is coated with a layer of material having chondrointegration properties.

The technology disclosed relates to methods of manufacturing an implant and a medical medical implant 1 for cartilage and/or bone repair at an articulating surface of a joint, comprising a contoured implant body 11 and at least one extending post 8, where said implant body has:
   a) an articulating surface 3 configured to face an articulating part of the joint;
   b) a bone contact surface 6 configured to face the bone structure of a joint, said articulating 3 and bone contact 6 surfaces facing mutually opposite directions; and
   c) a cartilage contact surface 7, which is a neighboring surface to the articulating surface 3 and connecting the articulating 3 and the bone contact 6 surfaces, and which is configured to contact the cartilage surrounding the implant body 11 in a joint, wherein the articulating surface 3 has an outer layer coating of wear-resistant material consisting of titanium nitride (TiN), and wherein said cartilage contact surface 7 is coated with a layer of material having chondrointegration properties for stimulating cartilage to grow into the implant surface.

The technology disclosed also relates to a method of manufacturing the medical implant 1 comprising:
- forming the implant body 11 of the implant 1, wherein the implant body 11 is consisting of titanium or a titanium-alloy;
- forming a wear-resistant layer on the articulating surface 3 of the implant body 11 of the medical implant 1, thereby making the articulating surface 3 harder and more durable, wherein said layer of wear-resistant material consists of titanium nitride (TiN) which is a coating material that adheres better to the titanium surface of the implant body 11 than other possible wear-resistant coatings, thereby mitigating the risk of cracking and/or delamination of the articulating surface 3 to provide a smoother transition to the cartilage contact surface 7; and
- forming a layer of material having chondrointegration properties on the cartilage contact surface 7 for stimulating cartilage to grow into the implant surface to achieve a firmer sealing and attachment of the implant, thereby providing a smoother transition between the cartilage and the implant leading to much lesser wear on the opposing surface of the joint as the cartilage and the implant work as an integrated mechanical entity with better resistance to destabilization by mechanical agitation or shear forces.

In embodiments, the technology disclosed relates to methods of manufacturing an implant and a medical implant 1 for cartilage and/or bone repair at an articulating surface of a joint, comprising a contoured implant body 11 and at least one extending post 8, where said implant body has:
- a) an articulating surface 3 configured to face an articulating part of the joint;
- b) a bone contact surface 6 configured to face the bone structure of a joint, where the bone contact surface 6 is provided with the at least one extending post (8), said articulating 3 and bone contact 6 surfaces facing mutually opposite directions; and
- c) a cartilage contact surface 7, which is a neighboring surface to the articulating surface 3 and connecting the articulating 3 and the bone contact 6 surfaces, and which is configured to contact the cartilage surrounding the implant body 11 in a joint, wherein
the articulating surface 3 has an outer layer coating of wear-resistant material consisting of titanium nitride (TiN) which is a coating material that adheres better to the titanium surface of the implant body 11 than other possible wear-resistant coatings, thereby mitigating the risk of cracking and/or delamination of the articulating surface 3 to provide a smoother transition to the cartilage contact surface 7, and wherein said cartilage contact surface 7 is coated with a layer of material having chondrointegration properties for stimulating cartilage to grow into the implant surface.

In embodiments, the technology disclosed relates to methods of manufacturing an implant and a medical implant 1 for cartilage and/or bone repair at an articulating surface of a joint, comprising a contoured implant body 11 and at least one extending post 8, where said implant body has:
- a) an articulating surface 3 configured to face an articulating part of the joint;
- b) a bone contact surface 6 configured to face the bone structure of a joint, where the bone contact surface 6 is provided with the at least one extending post 8, said articulating 3 and bone contact 6 surfaces facing mutually opposite directions; and
- c) a cartilage contact surface 7, which is a neighboring surface to the articulating surface 3 and connecting the articulating 3 and the bone contact 6 surfaces, and which is configured to contact the cartilage surrounding the implant body 11 in a joint, wherein the articulating surface 3 has an outer layer coating of wear-resistant material which provides for a harder, more durable and smoother surface than can be achieved with the titanium or titanium-alloy material used for the implant body 11, wherein said wear-resistant material consists of titanium nitride (TiN) which is a coating material that adheres better to the titanium surface of the implant body 11 than other possible wear-resistant coatings, thereby mitigating the risk of cracking and/or delamination of the articulating surface 3 to provide a smoother transition to the cartilage contact surface 7, and wherein said cartilage contact surface 7 is coated with a layer of material having chondrointegration properties for stimulating cartilage to grow into the implant surface, providing the effect of providing a smoother transition between the articulating surface 3 cartilage contact surface 7 and the synergistic effect of achieving a better adherence of the wear-resistant material coated on the articulating surface 3 to the titanium surface of the implant body.

In embodiments, the technology disclosed relates to a medical implant 1 for cartilage and/or bone repair at an articulating surface of a joint, comprising a contoured implant body 11 and at least one extending post 8, where said implant body has:
- a) an articulating surface 3 configured to face an articulating part of the joint;
- b) a bone contact surface 6 configured to face the bone structure of a joint, where the bone contact surface 6 is provided with at least one extending post 8, said articulating 3 and bone contact 6 surfaces facing mutually opposite directions; and
- c) a cartilage contact surface 7, which is a neighboring surface to the articulating surface 3 and connecting the articulating 3 and the bone contact 6 surfaces, which is configured to contact the cartilage surrounding the implant body 11 in a joint, wherein
the articulating surface 3 has an outer layer of wear-resistant material which is harder and more durable than the material used for the implant body 11, thereby providing a more even surface and a smoother transition to the neighboring cartilage contact surface 7, wherein said cartilage contact surface 7 is provided with a layer of material having chondrointegration properties for stimulating cartilage to grow into the implant surface, thereby providing a firmer sealing and attachment to the cartilage contact surface 7 and an even smoother transition to the neighboring articulating surface 3.

The layer of material having chondrointegration properties coated on the cartilage contact surface 7 for stimulating cartilage to grow into the implant surface also has the effect of providing a smoother transition between the articulating surface 3 cartilage contact surface 7.

In embodiments, the technology disclosed relates to method of manufacturing a medical implant 1, comprising:
- forming the implant body 11 and the at least one extending post 8 of the implant 1, wherein the implant body 11 and the at least one extending post 8 is consisting of titanium or a titanium-alloy; and forming a wear-resistant layer on the articulating surface 3 of the implant body 11 of the medical implant 1, wherein said layer of wear-resistant material is harder and more durable than the material used for the implant body 11, thereby providing a more even surface and a smoother transition to the neighboring cartilage contact surface 7; and forming a layer of material having chondrointegration properties on at least a portion of the cartilage contact surface 7 for stimulating cartilage to grow into the implant surface to achieve a firmer sealing and attachment of the implant, thereby providing a smoother transition between the cartilage and the implant leading to much lesser wear on the opposing surface of the joint as the cartilage and the implant work as an integrated mechanical entity with better resistance to destabilization by mechanical agitation or shear forces.

The forming of a layer of material having chondrointegration properties on at least a portion of the cartilage contact surface 7 for stimulating cartilage to grow into the implant surface also has the effect of providing a smoother transition between the articulating surface 3 cartilage contact surface 7.

Titanium nitride is a surface material which is hard and strong enough to withstand and tolerate the large mechanical forces and heavy and changing work loads subjected to it in the joint. Different grades exist where the properties have been optimised for applications in the human body. The inventors have understood that the pure titanium is softer than titanium nitride (TiN) and, in order to e.g. achieve a harder and more durable surface as well as a surface with a lower friction coefficient, a layer of titanium nitride (TiN) is provided, e.g. by depositing a suitable surface coating to the articulating surface 3. The articulating surface may subsequent the coating be polished to remove irregularities with the purpose of providing an even more even surface. The thickness of the wear-resistant layer of titanium nitride (TiN) which provided by coating the articulating surface (3) needs to be below 50 micrometer, preferably below 20 micrometer. If the wear-resistant layer of titanium nitride (TiN) is thicker than 50 micrometer, cracking and/or delamination of the coated layer may occur.

The present invention further relates to a new medical implant for replacing or repairing damaged, diseased or injured cartilage and underlying bone in an articulating surface of a joint. The implant has a cartilage contact surface, intended to contact the surrounding cartilage in a joint, which is coated with a material with chondrointegration properties which is capable of stimulating cartilage growth and regeneration. The implant alleviates problems discussed in the background, by promoting cartilage on-growth to the implant. By this feature the implant becomes more integrated with the cartilage surface, yielding a more stabilized interaction and firmer sealing and attachment between the implant and the cartilage. Thereby cartilage damage in the vicinity of the implant is decreased. Also, the entering of joint fluid between the implant, cartilage and bone is reduced or prevented. In addition, a smoother transition between the cartilage and the implant may be obtained, leading to lesser wear on the opposing surface of the joint as the cartilage and the implant works as an integrated mechanical entity.

The technology disclosed differs from the prior art in that:
1. the articulating surface of the implant is coated with a wear-resistant material consisting of titanium nitride (TiN), and that
2. the cartilage contact surface is coated with a layer of material having chondrointegration properties.

The technical effect of the first feature above of coating the articulating surface with a wear-resistant material consisting of titanium nitride (TiN) is that TiN as a coating material adheres better to the titanium surface of the implant body than other possible wear-resistant coatings. By adhering better to the titanium surface of the implant body, the risk of cracking and/or delamination of the articulating surface is mitigated which, in turn, provides a smoother transition to the cartilage contact surface.

The added feature of coating the articulating surface with TiN (rather than other possible wear-resistant coatings) to mitigate the risk of cracking and/or delamination provides the synergistic effect, or combinative effect, of further stimulating cartilage to grow into the implant surface when the cartilage contact surface is coated with a layer of material having chondrointegration properties.

Additional long-term synergistic effects of further stimulating cartilage to grow into the implant by mitigating the risk of cracking and/or delamination include achieving a smoother cartilage contact surface and thereby an even firmer sealing and attachment of the implant to the cartilage contact surface when a layer of material having chondrointegration properties is coated on the cartilage contact surface. This also provides the long-term synergistic effect of providing a smoother transition between the articulating surface and the neighboring cartilage contact surface, leading to a much lesser wear on the opposing surface of the joint as the cartilage and the implant continue to work as an integrated mechanical entity also in the long-term, with better resistance to destabilization by mechanical agitation or shear forces.

The technical effect of the second feature of coating the cartilage contact surface with a layer of material having chondrointegration properties coating is to stimulate cartilage to grow into the implant surface to achieve a firmer sealing and attachment of the implant, thereby providing for a smoother transition between the cartilage and the implant.

The long-term synergistic effects of coating the cartilage contact surface with a layer of material having chondrointegration properties include providing an even smoother transition between the cartilage contact surface and the articulating surface to maintain the improved adherence provided by the wear-resistant coating consisting of TiN which, in turn, leads to a much lesser wear on the opposing surface of the joint as the cartilage and the implant continues to work as an integrated mechanical entity in the long-term, with better resistance to destabilization by mechanical agitation or shear forces.

By coating the articulating surface 3 with a layer of wear-resistant material consisting of titanium nitride (TiN), rather than other possible wear-resistant coatings, mitigates or reduces the risk of cracking and/or delamination of the articulating surface (and the upper portion of the cartilage contact surface 7) at the peripheral edge of the articulating surface in the long-term, thereby providing a smoother transition/edge between the articulating surface and the cartilage contact surface 7 in the long-term. Achieving a smoother transition between the articulating surface 3 and the cartilage contact surface 7 by coating the articulating surface 3 with a titanium nitride (TiN) coating in turn has a synergistic effect in that the effect of the firmer sealing and attachment provided by the layer of material having chondrointegration properties coated on the cartilage contact surface is further improved.

Furthermore, coating a layer of material having chondrointegration properties on the cartilage contact surface 7 to achieve a firmer sealing and attachment of the implant to the surrounding cartilage also provides for a smoother transition between the articulating surface and the cartilage contact surface 7 in the long-term. Achieving a smoother transition between the articulating surface 3 and the cartilage contact surface 7 by coating a layer of material having chondrointegration properties on the cartilage contact surface 7 in turn has a synergistic effect in that the long-term effect of mitigating the risk of cracking and/or delamination of the articulating surface 3 by coating the articulating surface 3 with a titanium nitride (TiN) coating is further improved as the upper portion of the cartilage contact surface adheres better to the surrounding cartilage, thereby reducing the long-term risk of cracking and/or delamination of the articulating surface 3.

The implant of the technology disclosed comprises a contoured implant body 11, an articulating surface 3 adapted to face an articulating part of the joint, and a bone contact surface 6 adapted to face the bone structure of a joint. The articulating 3 and bone contact 6 surfaces of the implant are facing mutually opposite directions. The implant further comprises a cartilage contact surface 7 in form of a side edge surface, which is connecting the articulating 3 and the bone contact 6 surfaces. The cartilage contact surface 7 is adapted to contact the cartilage surrounding the implant body 11 in a joint. In embodiments, the bone contact surface 6 may be provided with at least one extending post 8.

In embodiments, the implant is provided with dual functionalities by having a first articulating surface 3 which is coated or modified to be more wear resistant and devised for facing the articulating part of the joint, and a second cartilage contact surface 7 which has chondrointegration properties and is devised for facing the surrounding cartilage. The layer of material provided on the articulating surface 3 provides a load bearing surface which is strong and hard enough to resist the wearing forces acting upon it through the relative movements within the joint. The cartilage contact surface 7 is provided with a material having osseointegration properties (bone), or chondrointegration properties (cartilage). The material promotes firm sealing and attachment to the cartilage contact surface 7.

In embodiments, the implant body comprises pure titanium (Ti), or a titanium-alloy, and the layer of material provided on the articulating surface, e.g. applied in a coating process, comprises titanium nitride (TiN) and the material with chondrointegration properties provided at least on the cartilage contact surface 7 comprises hydroxyapatite (HA). In certain embodiments, the coating may then be applied after fabrication, polishing and preliminary cleaning, by initially fixing the prosthesis on a rotating mount in a vacuum coating chamber. Following evacuation of the chamber, ionic surface cleaning may be achieved by striking an arc and producing a highly ionized titanium plasma.

In embodiments, the articulating surface of the new type of medical implant proposed by the inventors is coated with a wear-resistant material and at least the cartilage contact surface 7 is coated with a material with chondrointegration properties. The two coatings may then be applied concurrently to respective surface(s) or in a two-step process where the articulating surface 3 is coated with a wear-resistant material and at least the cartilage contact surface 7 is coated with a material having chondrointegration properties.

In embodiments, the articulating surface 3 of the medical implant proposed by the inventors is coated with a wear-resistant material and at least the cartilage contact surface 7 is coated with a material with chondrointegration properties. The two coatings may then be applied concurrently or the coating process may be divided into a two-step process where the articulating surface is coated with a wear-resistant material and the cartilage contact surface is coated with a material having chondrointegration properties.

As mentioned above, it has been observed that joint fluid may enter the small space between the implant and the cartilage, and flow into gaps between the bone and the implant. This may lead to a stopped or delayed integration between the bone and the implant. It may even lead to the undermining of the implant and to the detachment of the implant. Another problem that may arise is that the cartilage in the immediate vicinity of the implant may slide in relation to the implant, such that it is twisted, slides over the edge onto the top of the implant. The coating of an articulating surface implant body 11 made of titanium with a layer of titanium nitride (TiN) provides a surface which has a lower friction coefficient and which has less osseointegration properties, or chondrointegration properties.

If surrounding cartilage is allowed to slide over the edge, the provision of a layer of titanium nitride (TiN) on the articulating surface 3 when there is no coating of a material with chondrointegration properties on the cartilage contact surface 7 may, in the long-term, worsen the irregular cartilage formation and the wear damages to both the cartilage in the vicinity of the implant and to the cartilage on the opposing joint surface as the cartilage on top of the articulating surface 3 is more prone to move or glide on the articulating surface 3 due to the lower friction coefficient.

In embodiments, the implant body of the medical implant is comprised of pure titanium, or a titanium-alloy, and the articulating surface of the medical implant is coated with titanium nitride (TiN), which is a material which is harder and more wear-resistant than titanium.

In embodiments, the articulating surface 3 of a pure titanium implant is coated with titanium nitride (TiN) and at least the cartilage contact surface 7 of the implant is coated with a material with chondrointegration properties. The two coatings may then be applied concurrently, or the coating process may be a two-step process where the articulating implant is coated with a wear-resistant material and the cartilage contact surface 7 is coated with a material having chondrointegration properties.

In this disclosure, a material having osseointegration properties, or chondrointegration properties is a material that adheres, fuses or grows onto or into bone and cartilage. Osseointegration, or chondrointegration when it concerns cartilage, may also be defined as the formation of a direct interface between a surface and bone and/or cartilage, without intervening soft tissue. Osseointegration, or chondrointegration, may further be defined as the adherence of a surface to a bone and/or cartilage where the bone or cartilage is in direct contact with the surface and the interface surface between the surface and the bone and/or cartilage exhibits mechanical stability through increased friction, i.e., resistance to destabilization by mechanical agitation or shear forces.

If a certain material which have strong chondrointegration properties is provided on an articulating surface 3 facing an articulating part of a joint, this may cause strong shearing and friction forces in the interface surface between the articulating surface 3 and the cartilage surface of the opposed articulating part of the joint. This unwanted effect occurs because the increased adherence from the enhanced chondrointegration properties of the articulating surface 3 may negatively contribute to higher shear and friction for the relative movement between the articulating surface 3 and the opposing articulating part of the joint.

Osseointegration, or chondrointegration, may be defined as the formation of a direct interface between an implant and bone or bone, without intervening soft tissue. An osseointegrated implant is a type of implant that may be defined as an implant containing pores into which osteoblasts and supporting connective tissue can migrate. Applied to oral implantology, this thus refers to bone grown right up to the implant surface without interposed soft tissue layer. No scar tissue, cartilage or ligament fibers are present between the bone and implant surface.

A more recent definition defines osseointegration as a bone adherence where new bone is laid down directly on the implant surface and the implant exhibits mechanical stability, i.e., resistance to destabilization by mechanical agitation or shear forces. Osseointegration has enhanced the science of medical bone and joint replacement techniques and improving prosthetics for amputees.

The Implant Structure

Implant Structure in General

FIG. 1a shows an exemplifying embodiment of an implant 1 according to the present invention. The implant 1 comprises a contoured, substantially plate shaped implant body 11 and an extending post 8 extending from the implant body 11. The implant body 11 has an articulating surface 3, configured to face the opposing articulating part of the joint, and a bone contact surface 6, configured to face the bone structure of the joint. Between these surfaces of the plate shaped body 11 of the implant 1 there is a cartilage contact surface 7, on the rim or border that connects the articulating and the bone contact surfaces. The cartilage contact surface 7 is configured to face or contact the surrounding cartilage, and optionally also the bone, surrounding the implant when the implant is inserted in a joint such as a knee, ankle, toe, hip, elbow or shoulder. The articulating surface 3 is provided with a layer of wear-resistant material, such as titanium nitride (TiN) or zirconium nitride (ZrN) coating. In embodiments, at least one of the bone contact surface 6 and the cartilage contact surface 7 may be coated with a bioactive material having osseointegration properties (bone), or chondrointegration properties (cartilage), such as a hydroxyapatite coating.

The implant is placed in the joint after removal of the damaged cartilage and possibly also removal of damaged underlying bone and optionally, but preferably, after formation of a recess in the bone under the cartilage damage, e.g. by reaming or drilling. The implant is secured in the bone first by primary attachment, by means of the extending post 8 which fits in a drill hole in the bone, e.g. through press-fit or some locking mechanisms. The implant is also secured by a long-term secondary fixation mechanism where cartilage and/or bone tissue is grown into and/or onto the parts of the implant coated with bioactive material.

Details of the Implant Structure

Implant Body

The implant 1 comprises a contoured, substantially plate shaped implant body 11. The implant body 11 has a thin, plate-like design, meaning that its cross-sectional distance 9 is larger or even substantially larger than its thickness 4, e.g. at least 1.5 times larger. The plate can vary in size and shape and may be adjusted to the size and shape of the damaged cartilage tissue and to the needs of particular treatment situations. For instance, the cross-section of the implant body 11 may have a circular or roughly circular, oval, triangular, square or irregular shape, or a shape as two or more overlapping circles, preferably a shape without sharp edges. The size of the implant 1 may also vary. The surface area of the implant body 11 varies in different realizations of the invention between 0.5 cm$^2$ and 20 cm$^2$, between 0.5 cm$^2$ and 15 cm$^2$, between 0.5 cm$^2$ and 10 cm$^2$ or between about 1-10 cm$^2$, preferably between 0.5 cm$^2$ and 8 cm$^2$. In general, small implants are preferred since they have a smaller impact on the joint at the site of incision and are also more easily implanted which leads to smaller open surgical procedures. The primary factor for determining the size of the implant is however the nature of the lesion in the surface to be repaired. The thickness 4 of the implant body 11 is between 1 mm and about 20 mm, preferably between about 2 mm and 5 mm. The thickness of the implant body 11 should on the whole preferably match the thickness of the original cartilage layer, possibly also adapted to adjust for the recess in the bone, used for anchorage of the implant or formed as a part of the disease process. The thickness can possibly be adjusted it there is a bone lesion that may benefit from being replaced by the implant. The articulating implant surface and the cartilage surrounding the implant have, because of the prepared precise fit of the implant in the implant site, matching curvatures. The implant may be positioned slightly recessed into the surrounding cartilage (e.g. 0.5-1 mm).

Articulating Surface

The implant body 11 has an articulating surface 3 configured to face the opposing articulating part of the joint. The articulating surface 3 comprises a biocompatible metal, metal alloy or ceramic. More specifically it can consist of any metal or metal alloy used for structural applications in the human or animal body, such as stainless steel, cobalt-based alloys, chrome-based alloys, titanium-based alloys, pure titanium, zirconium-based alloys, tantalum, niobium and precious metals and their alloys. If a ceramic is used as the biocompatible material, it can be a biocompatible ceramic such as aluminium oxide, silicon nitride or yttria-stabilized zirconia. articulating.

It should also be understood that the articulating surface 3 may also be further surface treated in order to e.g. achieve an even more durable surface or a surface with a lower friction coefficient. Such treatments may include, for example, polishing, micro machining, heat treatment, precipitation hardening or depositing a suitable surface coating.

Titanium is a preferred material for the implant body 11 as it is a material which is well-proven clinically. Titanium and is also a material which is well-suited to be used in a 3D printing process for manufacturing a medical implant. Titanium is a much softer material than, for instance, cobalt chrome (CoCr), which is material widely used in implants, and titanium is therefore more suitable for use in a 3D printing process than cobalt chrome. In addition, titanium is also much easier to use as the production material in a 3D printing process than other possible implant materials such as alumina-zirconia composite or many other types of ceramics. Some titanium-alloys, e.g. Ti6Al4V, have similar properties as pure titanium and are therefore also suitable as the material for the implant body 11 for the same above reasons as pure titanium.

Furthermore, titanium and titanium-alloys have some osseointegration properties, or chondrointegration properties, so if a layer of osseointegration, or bioactive, material, which is provided on a surface to enhance the osseointegration properties of a bone and/or cartilage contact surface of an implant to stimulate bone and/or cartilage to grow into and/or onto the implant surface, delaminates or wears off with time, an implant body 11 comprising titanium beneath the delaminated or worn off layer of bioactive material can function as a back-up contact surface by providing some osseointegration properties, or chondrointegration properties, to the bone and/or cartilage contact surface when the bioactive material has delaminated and/or been worn off.

However, pure titanium or titanium alloys are not suitable to be used for the articulating surface of an implant because these materials are too soft and does not have the mechanical properties needed so that the articulating surface 3 can be sufficiently polished. Moreover, and as mentioned above, titanium is a material which integrates with cartilage, i.e. adheres well, fuses or grows into the cartilage, and is therefore unsuitable as material for the articulating surface 3 of the implant which is facing, and is occasionally in contact with, a cartilage surface of an opposing articulating part of the joint.

Generally, if a certain material which have strong chondrointegration properties is provided on an articulating surface 3 facing an articulating part of a joint, this may cause strong shearing and friction forces in the interface surface between the articulating surface 3 and the cartilage surface of the opposed articulating part of the joint. This unwanted effect occurs because the increased adherence from the enhanced chondrointegration properties of the articulating surface 3 may negatively contribute to higher shear and friction between the articulating surface 3 and the cartilage surface of the opposing articulating part of the joint when these two surfaces are in relative motion.

Titanium is thus rather unsuitable as the material for the articulating surface of an implant which is occasionally in contact with the cartilage surface of an opposing articulating part of the joint as it is not sufficiently wear-resistant material, but also due to its osseointegration properties, i.e. titanium is a material which adheres, fuses or grows into bone and cartilage. Osseointegration properties, or chondrointegration properties, are unsuitable for the material on the articulating surface 3 of the implant because the articulating surface 3 is facing, and is occasionally in contact with, an opposing cartilage surface of an articulating part of the joint which articulates, translates and/or rotates against the articulating surface of the implant.

Therefore, and according to certain aspects of the technology disclosed, the implant body 11 consists of titanium and the articulating surface 3 of the implant body needs to be provided with a wear-resistant layer to achieve at least one of a harder, a more durable surface and/or a surface with a lower friction coefficient than pure titanium. The inventors have found that an articulating surface 3 of an implant body 11 consisting of titanium requires a surface coating with a wear-resistant material to increase hardness, reduce wear and/or provide a surface with a lower friction coefficient. Preferably the articulating surface 3 is provided with a layer of titanium nitride (TiN), a ceramic material which is harder and more durable than titanium and can be provided to achieve a surface having a lower friction coefficient.

The inventors have found that medical implants provided with a layer of titanium nitride (TiN) that provides low friction, and highly wear-resistance would be especially useful in implants having an articulating surface facing an opposing articulating joint surface, such as in hip joints, knee joints, ankles, shoulders, elbows, etc.

According to embodiments, an implant body 11 consisting of titanium (Ti) is provided, e.g. coated, with a thin layer of titanium nitride (TiN) on its articulating surface 3. The inventors have found that titanium nitride (TiN) is a wear-resistant material which is harder and provides a more durable surface than titanium, and further that titanium nitride has a lower friction coefficient than titanium and is therefore more suitable as material for the articulating surface 3 facing, and occasionally being in direct contact with, a cartilage surface of the articulating part of the joint.

According to the technology disclosed, the inventors propose surface treatment of the titanium on the articulating surface 3 of the implant body 11 so that a thin layer of titanium nitride (TiN) is formed on the articulating surface 3, e.g. by depositing a surface coating of titanium nitride (TiN). The purpose of this surface treatment is to form a thin layer of titanium nitride (TiN) on the articulating surface 3 in order to provide an articulating surface which is harder, provides a more durable surface and have a lower friction coefficient than titanium, thereby providing for an articulating surface 3 of the implant that is more suitable for facing the cartilage surface of the articulating part of the joint.

The coating techniques which may be used for depositing titanium nitride include spray coating, thermal spraying, e.g. air plasma spraying, or Vacuum Plasma Spray coating (VPS).

To mitigate the risk of delamination of the articulating surface, the titanium nitride layer on the articulating surface may be provided by modifying the titanium surface using e.g. a nitrogen-containing gas or alloys instead of surface coating the articulating surface.

In embodiments, titanium nitride coating (TiN-coating) is applied on the articulating surface 3 of the implant body 11. The purpose and technical effect of the TiN-coating is to make the articulating surface 3 of the implant body 11 harder and more durable, and, additionally, provide a surface with a lower friction coefficient as the TiN-coating provides the articulating surface 3 with the mechanical properties needed to achieve sufficient polishing of the articulating surface 3.

In other embodiments, ceramic oxides and nitrides are also are also possible to use for the layer of material provided on the articulating surface 3 of the implant, but are less favorable when the material of the implant body 11 is pure titanium or some of the titanium-alloys.

The titanium nitride (TiN) is the preferred material for coating an implant surface made of titanium, or titanium-alloys, to provide an articulating surface which is harder, wear-resistant, easier to polish and has a lower friction coefficient than titanium. Titanium nitride (TiN) is a preferred material compared to, for example, zirconium nitride (ZrN), as the risk of delamination of a wear-resistant layer provided on an articulating surface of an implant made of titanium is mitigated by coating the titanium surface with titanium nitride (TiN) compared to coating the titanium surface with, for example, zirconium nitride (ZrN).

The articulating surface 3 of the implant body 11 of the implant 1 may also be provided with a layer of zirconium nitride (ZrN). Zirconium nitride (ZrN) is a hard coating, somewhat harder than TiN, but otherwise very similar in nature. It is currently used on cutting blocks, but to a lesser degree than titanium nitride (TiN), as it is more expensive to deposit. In current applications, ZrN is often applied in a Physical Vapor Deposition coating (PVD) process. The coating techniques which may be used for depositing titanium nitride also include spray coating, thermal spraying, e.g. air plasma spraying, Vacuum Plasma Spray coating (VPS).

The medical implant (1) which is provided with a layer of zirconium nitride (ZrN), or ceramic oxides and nitrides, is then adapted for cartilage and/or bone repair at an articulating surface of a joint, comprising a contoured, substantially plate shaped, implant body (11) and at least one extending post (8), where said implant body has:

a) an articulating surface (3) configured to face the articulating part of the joint;
b) a bone contact surface (6) configured to face the bone structure of a joint, where the bone contact surface (6) is provided with the extending post (8), said articulating (3) and bone contact (6) surfaces facing mutually opposite directions; and
c) a cartilage contact surface (7), connecting the articulating (3) and the bone contact (6) surfaces, which is configured to contact the cartilage surrounding the implant body (11) in a joint, wherein the articulating surface 3 of the implant body (11) is provided with a layer of zirconium nitride (ZrN), or ceramic oxides or nitrides.

In example embodiments, the implant body 11 consists of titanium (Ti) and the articulating surface 3 of the implant body 11 is provided with a layer of zirconium nitride (ZrN), or a layer of ceramic oxides or nitrides.

Bone Contact Surface

The implant body 11 has a bone contact surface 6, configured to face or contact the bone structure of the joint. In one embodiment the bone contact surface 6 comprises a biocompatible metal, metal alloy or ceramic, such as any of the metals, metal alloys or ceramic described above for the articulating surface 3.

In one embodiment the bone contact surface 6 comprises, or in one specific embodiment is coated with, a material with osseointegration properties. In an alternative embodiment of the invention, the bone contact surface does not comprise a material with osseointegration properties and/or is uncoated. Preferably, the bone contact surface 6 is provided with a layer of hydroxyapatite (HA).

The bioactive material of the bone contact surface, if present, preferably stimulates bone to grow into and/or onto the implant surface. Several bioactive materials that have a stimulating effect on bone growth are known and have been used to promote adherence between implants and bone. Examples of such prior art bioactive materials include bioactive glass, bioactive ceramics and biomolecules such as collagens, fibronectin, osteonectin and various growth factors, e.g. bone morphogenetic protein (BMP). A commonly used bioactive material in the field of implant technology is the bioactive ceramic hydroxyapatite (HA), chemical formula $Ca_{10}(PO_4)_6(OH)_2$. HA is the major mineral constituent of bone and is able to slowly bond with bone in vivo. Thus, HA coatings have been developed for medical implants to promote bone attachment. Other bioactive ceramics include calcium sulphate, calcium phosphate, calcium aluminates, calcium silicates, calcium carbonates or combinations thereof, or bioactive glass. Bioactive glasses, generally comprising $SiO_2$, $CaSiO_3$, $P_2O_5$, $Na_2O$ and/or CaO and possibly other metal oxides or fluorides, are able to stimulate bone growth faster than HA.

The bioactive materials described above have an anabolic effect on the bone i.e. stimulates bone growth. The fixation of the implant can also be improved by decreasing the catabolic processes i.e. decrease the amount of bone resorption next to the implant. The bone contact surface 21 and/or the extending post can also be modified with bisphosphonates. Bisphosphonates are substances that inhibit the catabolic process of bone. One way to bind the bisphosphonate to the surface is by coating it with HA, which it readily binds to. The implant can also simply be immersed in a bisphosphonate solution or linked with some other biocompatible molecule e.g. carbodiimides, N-hydroxysuccinimide (NHS)-esters, fibrinogen, collagen etc.

The bone contact surface may also be further modified with fluoro compounds to enhance the bioactivity of the surface.

Polyether ether ketone (PEEK) possesses excellent mechanical properties similar to those of human bone and is considered the best alternative material other than titanium or titanium-alloys for the implant body 11 orthopedic spine and trauma implants. However, the deficient osteogenic properties and the bioinertness of PEEK limit its fields of application. These drawbacks may be limited by coating the surface of PEEK with hydroxyapatite (HA).

However, PEEK has shown both in vivo and in vitro studies to have low bioactive features due to the relatively bioinert surface. Therefore, many studies have been conducted to improve the biocompatible state of PEEK by incorporating bioactive substances into the substrate or onto the surface as a coating. It has been observed that incorporation of hydroxyapatite (HA) into the PEEK compound substantially decreased the mechanical properties of the material. Instead, by altering the surface topography and chemical composition, the surface becomes more bioactive and an improved bone formation can be achieved owing to an increased surface area and higher surface energy 3. Therefore, several techniques to coat the PEEK surface have been evaluated. Plasma sprayed deposition and electron beam deposition are two common methods to coat the surface with HA, which improved the bioactive potential of PEEK. However, the long-term effect of these techniques on titanium has been questioned after retrieved sections have demonstrated inflammation cells adjacent to detached coating fragments. The coating thickness and mechanical attachment to the substrate were hypothesized to be one reason to cause this incident.

In embodiments of the present invention, at least one of the cartilage contact surface 7 and the bone contact surface 6 of an implant body consisting of Polyether ether ketone (PEEK) is coated with a double coating. Such double coating may for instance comprise an inner coating comprising titanium (Ti). The second, outer coating, that is configured to contact the bone and/or cartilage, is preferably a HA coating, e.g. containing more than 95% HA or 95-99.5% HA, or a coating comprising tricalcium phosphate (TCP) in combination with HA. By this design even more long-term fixation of the implant is achieved, since bone in- or on-growth to the implant is further stimulated by the titanium, even if the more brittle and/or soluble HA and/or TCP would eventually shed or dissolve.

Cartilage Contact Surface

Between the articulating surface 3 and the bone contact surface 6 of the substantially plate shaped body 11 there is a cartilage contact surface 7 on the rim or border which connects the articulating and the bone contact surfaces. The cartilage contact surface 7 is configured to face or contact the cartilage surrounding the implant and optionally also the bone underlying the cartilage layer when the implant is inserted in a joint for example in the knee. The cartilage contact surface 7 is coated with a bioactive material, such as any of bioactive materials described above for the bone contact surface 6. Preferably the material with chondrointegration properties is capable of stimulating cartilage growth, regeneration and attachment. A surface with chondrointegration properties promotes adhesion of the implant to the surrounding cartilage surface. Such materials include hydroxyapatite (HA), titanium (Ti), bone morphogenetic protein (BMP) or beta tricalcium phosphate (TCP), separately or in combination. In certain embodiments of the technology disclosed, the material with chondrointegration properties provided on the cartilage contact surface 7 is hydroxyapatite (HA) and/or beta tricalcium phosphate (TCP).

In embodiments, the cartilage contact surface 7 is coated with a double coating, such as described for the bone contact surface 6 above. Such double coating may for instance comprise an inner coating comprising titanium (Ti). The second, outer coating, that is configured to contact the bone, is preferably a HA coating containing more than 95% HA or 95-99.5% HA, or a coating comprising tricalcium phosphate (TCP), or a combination of HA and TCP.

Using a bioactive material such as hydroxyapatite as a coating on the cartilage contact surface 7 of the implant has the effect that the implant, after insertion at the implant site with primary fixation, is fixated by a secondary fixation mechanism where the cartilage grows together with the bioactive coating of the implant, creating a smooth sealed surface without any holes or where joint fluid can pass. This would lead to an implant that stays in the right place and that is not prone to be undermined by joint fluids. Also, the smooth surface, where the implant and the surrounding cartilage may act as an integrated mechanical entity, reduces or prevents wear damage on the surface of the opposing side of the joint.

The height 4 of the cartilage contact surface 7 corresponds to at least 75% of the thickness of the cartilage at the site of implant insertion in the joint. More preferably the height 4 of the cartilage contact surface 7 corresponds to the height of the cartilage surrounding the implant site plus the height of an area reamed/drilled out from the underlying bone in order to fit and fix the implant. The height 4 of the cartilage contact surface 7 may vary between said extremes. Typically, the height 4 of the cartilage contact surface 7 is between 0.5 and 20 mm, preferably between 2 and 15 mm.

The bioactive coating on the cartilage contact surface 7 is preferably provided all the way around the cartilage contact surface 7 on the rim of the plate shaped implant body 11. The coating is intended to be in direct contact with the surrounding cartilage and bone of a joint once the implant is implanted in the cartilage of a joint, for example a knee. The coating covers 60-100%, more preferably 80-100% and most preferably 90-100% of the cartilage contacting surface 7. In another embodiment the surface is coated such that the height 4 all around the rim of the implant body 11 is 80-100%, preferably 90-100% covered, counting from the bone contact surface 6 and upwards. In still another embodiment the coating covers most of the cartilage contact surface 7, except for an uncoated section 0.5-1 mm at the top of the height 4, adjacent to the articulating surface 3. By keeping the section closest to the articulating surface uncoated shedding of the bioactive material onto the cartilage surface surrounding the implant is prevented/reduced, thereby reducing the risk of wear from the shed material onto the joint surfaces.

The coating technique used is preferably thermal spraying; in particular, air plasma spraying is the method which is used for producing these hydroxyapatite coatings on the implant. Another alternative is Vacuum Plasma Spray coating (VPS). In a hydroxyapatite embodiment the coating contains more than 95% hydroxyapatite by X-ray Diffraction (XRD) analysis after treatment or alternatively the coating or the hydroxyapatite coating contains 95-99.5% hydroxyapatite.

Extending Post

The implant body 11 may have one or several extending posts 8 which extend from the bone contact surface 6. In order to promote an immediate attachment of the implant to the bone as it is implanted into the body, the extending post 8 is used for immediate, mechanical attachment, called primary fixation. The extending post 8 has a physical structure in the form of for example a cylinder or other shapes such as one or more of a small screw, peg, keel, barb or the like. The implant body 11 and the extending post(s) 8 may be manufactured as a single, integral piece or as separate pieces that are joined by some kind of attachment means, e.g. glue or by a threaded joint.

The primary fixation means 4 may comprise e.g. the metal, metal alloy or ceramic, as in the articulating surface 3.

The extending post 8 can in one aspect of the invention be coated with a bioactive material such as described for the bone contact surface 6 above. In another aspect of the invention the extending post is uncoated.

In one embodiment the extending post 8 comprises uncoated titanium (Ti) and the cartilage contact surface 7 are coated with hydroxyapatite (HA) or a double coating with an inner coating and an outer coating comprising HA, tricalcium phosphate (TCP), or a combination of HA and TCP.

An implant which does not have a coating on the extending post 8, and thus lacks a secondary fixation of the extending post, is suitable for repairing a cartilage damage in for example a hip joint where a lot of pressure is applied on the placed implant and where there is a need for an implant which reduces the risk for tensions when the mechanical pressure is high. By avoiding coating of the extending post, the extending post is thus not attached to the bone; the mechanical forces are in this way not directed into the bone part through the extending post (which may lead to tensions in the bone structure). The mechanical forces are directed to the bone through the implant head only which reduces the risk for tensions in the bone on the implant site.

Manufacturing of the Implant

An implant according to the present invention may be manufactured in predetermined, standard shapes and sizes or be tailor made for specific patients. A variety of manufacturing processes are conceivable, including, casting, molding, sintering or turning/cutting a blank e.g. with laser etc.

According to certain of the example embodiments, the medical implant 1 may be manufactured by a 3D printing process in which material is joined or solidified under computer control to create the medical implant. The method of manufacturing by a 3D printing process may include building the medical implant from computer-aided design (CAD) data by successively adding material layer by layer. The CAD data may further be based on a virtually designed 3D model obtained from a medical image of at least a part of a joint. In certain embodiments, the implant is a patient matched, or even a patient specific, implant based on obtained image data of a patient's joint.

Certain aspects of the technology disclosed describes a method of manufacturing the medical implant 1, comprising manufacturing at least portions of at least one of the implant body 11 and the at least one extending post 8 of the medical implant 1 based on design parameters, wherein said manufacturing of the medical implant 1 includes forming a layer of wear-resistant layer on the articulating surface 3 of the implant body 11 of the medical implant for the purpose of making the articulating surface 3 harder and more durable.

In certain embodiments, the manufacturing of the implant body 11 is a 3D printing process in which titanium, or a titanium-alloys, is used to form at least one of the implant body 11 and the extending post, and a layer of titanium nitride (TiN) is formed on the articulating surface 3 of the implant body 11 as part of said 3D printing process.

In certain embodiments, manufacturing of the implant body 11 is a 3D printing process in which a layer of bioactive material is formed on at least one of a bone contact surface 6, a cartilage contact surface 7 and at least portions of at least one extending post 8 as part of said 3D printing process.

According to certain embodiments, the medical implant is patient-matched, or patient-customized, via imagery of the patient's joint through at least one medical image, e.g. an MRI, CT, X-ray or ultrasound image, thereby providing for one of a patient-matched or a patient-customized medical implant.

According to embodiments, the above method of manufacturing the medical implant 1 in a 3D printing process may preceded by the following steps of designing a medical implant:

obtaining, through medical images such as MR, CT, X-ray or ultrasound images, image data representing a three-dimensional image of at least a portion of a joint; identifying, in the obtained image data, a bone and/or cartilage damage in an articulating surface of the joint;

determining, based on the obtained image data, the location, shape and/or size of the bone and/or cartilage damage;

determining, based on the obtained image data, the surface contour curvature of the cartilage and/or the subchondral bone in the joint in a predetermined area comprising and surrounding the site of the bone and/or cartilage damage; and generating, based on the obtained image data, design parameters for the medical implant, including generating the contour curvature for an articulating surface 3 of a substantially plate shaped implant body dependent on said determined surface curvature of the cartilage and/or the subchondral bone.

In one embodiment according to the present invention the articulating surface 3 may be formed in a way so that it substantially corresponds to the curvature of the articulating surface at the site of the diseased cartilage but prior to damage and such that it is adapted to a particular individual and its cartilage damage. Techniques for obtaining such 3D images, of either the cartilage or the underlying bone or both may also include X-rays, optical coherence tomography, SPECT, PET, MR and ultrasound imaging techniques. The 3D images are used for measuring the reconstruction of the bone and the thickness and/or curvature of the cartilage and for determining the position, size and contour of damaged cartilage or cartilage loss.

A technique for making these tailor made implants is selective laser sintering (SLS). SLS is an additive manufacturing technique that uses a high power laser (for example, a carbon dioxide laser) to fuse small particles of plastic, metal (Direct metal laser sintering), ceramic, or glass powders into a mass representing a desired 3-dimensional object. The laser selectively fuses powdered material by scanning cross-sections generated from a 3-D digital description of the part (for example from a CAD file or scan data) on the surface of a powder bed. After each cross-section is scanned, the powder bed is lowered by one layer thickness, a new layer of material is applied on top, and the process is repeated until the part is completed. Or, the 3D surfaces are formed with a high precision lathe, a machine in which work is rotated about a horizontal axis and shaped by a fixed tool. The 3D surfaces can also be reamed using the digital data

The invention claimed is:

1. A medical implant for cartilage and/or bone repair at an articulating surface of a joint, comprising a contoured implant body and at least one extending post, where said implant body has:

a) an articulating surface configured to face an articulating part of the joint;
b) a bone contact surface configured to face the bone structure of a joint, said articulating and bone contact surfaces are opposing surfaces; and
c) a cartilage contact surface, which is an adjoining surface to the articulating surface and connecting the articulating and the bone contact surfaces, and which is configured to contact the cartilage surrounding the implant body in a joint, wherein the implant is a surface implant and the implant body is made of titanium and is coated with two different coatings on separate adjoining surfaces, one of the two different coatings is on the articulating surface and includes wear-resistant material consisting of titanium nitride (TiN), the other of the two different coatings is on said cartilage contact surface and includes material having chondrointegration properties for stimulating cartilage to grow into the implant surface, wherein the material having chondrointegration properties is coated on 60-90% of the cartilage contact surface area.

2. The medical implant of claim 1, wherein said material having chondrointegration properties is any of hydroxyapatite (HA), bone morphogenetic protein (BMP), beta tricalcium phosphate (TCP), alfa tricalcium phosphate (TCP), collagens, fibronectin, osteonectin, calcium sulphate, calcium phosphate, calcium aluminates, calcium silicates, calcium carbonates or bioactive glass, fluoro compounds or combinations thereof.

3. The medical implant according to claim 1, wherein said bone contact surface is coated or partly coated with a material having osseointegration properties.

4. The medical implant according to claim 1, wherein said extending post is coated or partly coated with a material having osseointegration properties.

5. The medical implant according claim 1, wherein at least part of said extending post is not coated with bioactive material.

6. The medical implant according to claim 1, wherein said articulating surface substantially corresponds to curvature of the articulating surface at a site of diseased cartilage.

7. The medical implant according to claim 1, wherein the cartilage contact surface and/or bone contact surface and/or extending post has a coating consisting of more than 95% hydroxyapatite.

8. A medical implant for cartilage and/or bone repair at an articulating surface of a joint, comprising a contoured implant body and at least one extending post, where said implant body has:

d) an articulating surface configured to face an articulating part of the joint;
e) a bone contact surface configured to face the bone structure of a joint, said articulating and bone contact surfaces are opposing surfaces; and
f) a cartilage contact surface, which is an adjoining surface to the articulating surface and connecting the articulating and the bone contact surfaces, and which is configured to contact the cartilage surrounding the implant body in a joint, wherein the implant is a surface implant and the implant body is made of titanium and is coated with two different coatings on separate adjoining surfaces, one of the two different coatings is on the articulating surface and includes wear-resistant material consisting of titanium nitride (TiN), the other of the two different coatings is on said cartilage contact surface and includes material having chondrointegration properties for stimulating cartilage to grow into the implant surface, wherein the cartilage contact surface includes an uncoated section nearest the articulating surface.

* * * * *